US011945844B2

(12) United States Patent
Samish et al.

(10) Patent No.: US 11,945,844 B2
(45) Date of Patent: Apr. 2, 2024

(54) TASTE AND FLAVOR-MODIFIER PROTEINS

(71) Applicant: AMAI PROTEINS LTD., Rehovot (IL)

(72) Inventors: Ilan Samish, Ness-Ziona (IL); Itamar Kass, Kfar-Yona (IL); Dalit Hecht, Rehovot (IL)

(73) Assignee: AMAI PROTEINS LTD., Rehovot (IL)

( * ) Notice: Subject to any disclaimer, the term of this patent is extended or adjusted under 35 U.S.C. 154(b) by 0 days.

(21) Appl. No.: 17/053,687

(22) PCT Filed: May 6, 2019

(86) PCT No.: PCT/IL2019/050510
§ 371 (c)(1),
(2) Date: Nov. 6, 2020

(87) PCT Pub. No.: WO2019/215730
PCT Pub. Date: Nov. 14, 2019

(65) Prior Publication Data
US 2021/0139546 A1    May 13, 2021

Related U.S. Application Data

(60) Provisional application No. 62/667,532, filed on May 6, 2018.

(51) Int. Cl.
*C07K 14/43*      (2006.01)
*A23L 27/30*      (2016.01)
*A23L 33/18*      (2016.01)

(52) U.S. Cl.
CPC .............. *C07K 14/43* (2013.01); *A23L 27/31* (2016.08); *A23L 33/18* (2016.08)

(58) Field of Classification Search
CPC .......... C07K 14/43; A23L 27/31; A23L 33/18
See application file for complete search history.

(56) References Cited

U.S. PATENT DOCUMENTS 5,234,834 A * 8/1993 Fischer .............. C12N 15/8242
536/23.6
2020/0399379 A1   12/2020 Govindappa et al.

FOREIGN PATENT DOCUMENTS

| CN | 109627307 A | 4/2019 |
|---|---|---|
| GB | 2123672 | 2/1984 |
| KR | 20120052542 A | 5/2012 |
| RU | 2015140608 | 4/2017 |
| WO | 8402450 | 7/1984 |

OTHER PUBLICATIONS

Aghera et al., "A Buried Ionizable Residue Destabilizes the Native State and the Transition State in the Folding of Monellin", 2012, Biochemistry, vol. 51, pp. 9058-9066 (Year: 2012).*
Jonson, P.H., Petersen, S.B., "A critical view on conservative mutations", 2001, Protein Engineering, vol. 14, No. 6, pp. 397-402 (Year: 2001).*
Leone et al., "Sweeter and stronger: enhancing sweetness and stability of the single chain monellin MNEI through molecular design", Scientific Reports, vol. 6, No. 1, Sep. 23, 2016.
Weiwei et al., "Expression purification and characterization of a novel double-sites mutant of the single-chain sweet-lastin protein monellin (MNEI) with both improved sweetness and stability", Protein Expression and Purifications, vol. 143, Mar. 1, 2018, pp. 52-56.
International Search Report and Written Opinion dated Jul. 22, 2019 in corresponding International Patent Application No. PCT/IL2019/050510.
Meng et al., "Structure basis of the improved sweetness and thermostability of a unique double-sites single-chain sweet-tasting protein monellin (MNEI) mutant", Biochimie, Masson, Paris, FR, vol. 154, Sep. 6, 2018, pp. 156, 163.
Pica, et al., "pH driven fibrillar aggregation of the super-sweet protein Y65R-MNEI: A step-bystep structural analysis", Biochimica Et Biophysica Acta (BBA)—General Subjects, vol. 1862, No. 4, Apr. 1, 2018, pp. 808-815.
Liu et al., "Modification of the Sweetness and Stability of Sweet-Tasting Protein Monellin by Gene Mutation and Protein Engineering", Biomed Research International, vol. 2016, Jan. 1, 2016, pp. 1-7.
Esposito et al., "The Importance of Electrostatic Potential in the Interaction of Sweet Proteins with the Sweet Taste Receptor", Journal of Molecular Biology, Academic Press, United Kingdom, vol. 360, No. 2, Jul. 7, 2006, pp. 448-456.
Rega, Design of sweet protein based sweeteners: Hints from structure-function relationships, Food Chemistry, (2015), pp. 1179-1186, vol. 173, Elsevier, Ltd.

* cited by examiner

*Primary Examiner* — Jeffrey P Mornhinweg
*Assistant Examiner* — Kelly P Kershaw
(74) *Attorney, Agent, or Firm* — The Roy Gross Law Firm, LLC; Roy Gross

(57) ABSTRACT

The present invention relates to a modified protein comprising an amino acid sequence that has one or more amino acids replacements from a reference protein, wherein the modified protein has at least one improved food-related property compared to the reference protein and to uses thereof in the food industry.

9 Claims, 3 Drawing Sheets

Specification includes a Sequence Listing.

SEQUENCE LISTING

<160> NUMBER OF SEQ ID NOS: 32

<210> SEQ ID NO 1
<211> LENGTH: 207
<212> TYPE: PRT
<213> ORGANISM: Thaumatococcus daniellii
<220> FEATURE:
<221> NAME/KEY: MISC_FEATURE
<223> OTHER INFORMATION: Thaumatin I GenBank Entry No. P02883

<400> SEQUENCE: 1

```
Ala Thr Phe Glu Ile Val Asn Arg Cys Ser Tyr Thr Val Trp Ala Ala
1               5                   10                  15
Ala Ser Lys Gly Asp Ala Ala Leu Asp Ala Gly Gly Arg Gln Leu Asn
            20                  25                  30
Ser Gly Glu Ser Trp Thr Ile Asn Val Glu Pro Gly Thr Asn Gly Gly
        35                  40                  45
Lys Ile Trp Ala Arg Thr Asp Cys Tyr Phe Asp Asp Ser Gly Ser Gly
    50                  55                  60
Ile Cys Lys Thr Gly Asp Cys Gly Gly Leu Leu Arg Cys Lys Arg Phe
65                  70                  75                  80
Gly Arg Pro Pro Thr Thr Leu Ala Glu Phe Ser Leu Asn Gln Tyr Gly
                85                  90                  95
Lys Asp Tyr Ile Asp Ile Ser Asn Ile Lys Gly Phe Asn Val Pro Met
            100                 105                 110
Asn Phe Ser Pro Thr Thr Arg Gly Cys Arg Gly Val Arg Cys Ala Ala
        115                 120                 125
Asp Ile Val Gly Gln Cys Pro Ala Lys Leu Lys Ala Pro Gly Gly Gly
    130                 135                 140
Cys Asn Asp Ala Cys Thr Val Phe Gln Thr Ser Glu Tyr Cys Cys Thr
145                 150                 155                 160
Thr Gly Lys Cys Gly Pro Thr Glu Tyr Ser Arg Phe Phe Lys Arg Leu
                165                 170                 175
Cys Pro Asp Ala Phe Ser Tyr Val Leu Asp Lys Pro Thr Thr Val Thr
            180                 185                 190
Cys Pro Gly Ser Ser Asn Tyr Arg Val Thr Phe Cys Pro Thr Ala
        195                 200                 205
```

<210> SEQ ID NO 2
<211> LENGTH: 234
<212> TYPE: PRT
<213> ORGANISM: Thaumatococcus daniellii
<220> FEATURE:
<221> NAME/KEY: MISC_FEATURE
<223> OTHER INFORMATION: Thaumatin-2 GenBank Entry No. P02884

<400> SEQUENCE: 2

```
Met Ala Ala Thr Thr Cys Phe Phe Phe Leu Phe Pro Phe Leu Leu Leu
1               5                   10                  15
Leu Thr Leu Ser Arg Ala Ala Thr Phe Glu Ile Val Asn Arg Cys Ser
            20                  25                  30
Tyr Thr Val Trp Ala Ala Ala Ser Lys Gly Asp Ala Ala Leu Asp Ala
        35                  40                  45
Gly Gly Arg Gln Leu Asn Ser Gly Glu Ser Trp Thr Asn Val Glu Pro
    50                  55                  60
Gly Thr Lys Gly Gly Lys Ile Trp Ala Arg Thr Asp Cys Tyr Phe Asp
65                  70                  75                  80
Asp Ser Gly Arg Gly Ile Cys Arg Thr Gly Asp Cys Gly Gly Leu Leu
                85                  90                  95
Gln Cys Lys Arg Phe Gly Arg Pro Pro Thr Thr Leu Ala Glu Phe Ser
            100                 105                 110
Leu Asn Gln Tyr Gly Lys Asp Tyr Ile Asp Ile Ser Asn Ile Lys Gly
        115                 120                 125
Phe Asn Val Pro Met Asp Phe Ser Pro Thr Thr Arg Gly Cys Arg Gly
    130                 135                 140
```

Val Arg Cys Ala Ala Asp Ile Val Gly Gln Cys Pro Ala Lys Leu Lys
145                 150                 155                 160

Ala Pro Gly Gly Gly Cys Asn Asp Ala Cys Thr Val Phe Gln Thr Ser
            165                 170                 175

Glu Tyr Cys Cys Thr Thr Gly Lys Cys Gly Pro Thr Glu Tyr Ser Arg
            180                 185                 190

Phe Phe Lys Arg Leu Cys Pro Asp Ala Phe Ser Tyr Val Leu Asp Lys
            195                 200                 205

Pro Thr Val Thr Cys Pro Gly Ser Ser Asn Tyr Arg Val Thr Phe
            210                 215                 220

Cys Pro Thr Ala Leu Glu Leu Glu Asp Glu
225                 230

<210> SEQ ID NO 3
<211> LENGTH: 45
<212> TYPE: PRT
<213> ORGANISM: Dioscoreophyllum cumminsii
<220> FEATURE:
<221> NAME/KEY: MISC_FEATURE
<223> OTHER INFORMATION: Monellin chain A GenBank Entry No. P02881

<400> SEQUENCE: 3

Phe Arg Glu Ile Lys Gly Tyr Glu Tyr Gln Leu Tyr Val Tyr Ala Ser
1               5                   10                  15

Asp Lys Leu Phe Arg Ala Asp Ile Ser Glu Asp Tyr Lys Thr Arg Gly
            20                  25                  30

Arg Lys Leu Leu Arg Phe Asn Gly Pro Val Pro Pro
        35                  40                  45

<210> SEQ ID NO 4
<211> LENGTH: 50
<212> TYPE: PRT
<213> ORGANISM: Dioscoreophyllum cumminsii
<220> FEATURE:
<221> NAME/KEY: MISC_FEATURE
<223> OTHER INFORMATION: Monellin chain B GenBank Entry No. P02882

<400> SEQUENCE: 4

Gly Glu Trp Glu Ile Ile Asp Ile Gly Pro Phe Thr Gln Asn Leu Gly
1               5                   10                  15

Lys Phe Ala Val Asp Glu Glu Asn Lys Ile Gly Gln Tyr Gly Arg Leu
            20                  25                  30

Thr Phe Asn Lys Val Ile Arg Pro Cys Met Lys Lys Thr Ile Tyr Glu
        35                  40                  45

Glu Asn
    50

<210> SEQ ID NO 5
<211> LENGTH: 96
<212> TYPE: PRT
<213> ORGANISM: Artificial Sequence
<220> FEATURE:
<223> OTHER INFORMATION: Monelin MNEI

<400> SEQUENCE: 5

Gly Glu Trp Glu Ile Ile Asp Ile Gly Pro Phe Thr Gln Asn Leu Gly
1               5                   10                  15

Lys Phe Ala Val Asp Glu Glu Asn Lys Ile Gly Gln Tyr Gly Arg Leu
            20                  25                  30

Thr Phe Asn Lys Val Ile Arg Pro Cys Met Lys Lys Thr Ile Tyr Glu
        35                  40                  45

```
Asn Glu Gly Phe Arg Glu Ile Lys Gly Tyr Glu Tyr Gln Leu Tyr Val
     50                  55                  60

Tyr Ala Ser Asp Lys Leu Phe Arg Ala Asp Ile Ser Glu Asp Tyr Lys
 65                  70                  75                  80

Thr Arg Gly Arg Lys Leu Leu Arg Phe Asn Gly Pro Val Pro Pro Pro
                 85                  90                  95
```

<210> SEQ ID NO 6
<211> LENGTH: 220
<212> TYPE: PRT
<213> ORGANISM: Synsepalum dulcificum
<220> FEATURE:
<221> NAME/KEY: MISC_FEATURE
<223> OTHER INFORMATION: Miraculin GenBank Entry No. P13087

<400> SEQUENCE: 6

```
Met Lys Glu Leu Thr Met Leu Ser Leu Ser Phe Phe Phe Val Ser Ala
 1               5                  10                  15

Leu Leu Ala Ala Ala Ala Asn Pro Leu Leu Ser Ala Ala Asp Ser Ala
                 20                  25                  30

Pro Asn Pro Val Leu Asp Ile Asp Gly Glu Lys Leu Arg Thr Gly Thr
             35                  40                  45

Asn Tyr Tyr Ile Val Pro Val Leu Arg Asp His Gly Gly Gly Leu Thr
 50                  55                  60

Val Ser Ala Thr Thr Pro Asn Gly Thr Phe Val Cys Pro Pro Arg Val
 65                  70                  75                  80

Val Gln Thr Arg Lys Glu Val Asp His Asp Arg Pro Leu Ala Phe Phe
                 85                  90                  95

Pro Glu Asn Pro Lys Glu Asp Val Val Arg Val Ser Thr Asp Leu Asn
             100                 105                 110

Ile Asn Phe Ser Ala Phe Met Pro Cys Arg Trp Thr Ser Ser Thr Val
         115                 120                 125

Trp Arg Leu Asp Lys Tyr Asp Glu Ser Thr Gly Gln Tyr Phe Val Thr
     130                 135                 140

Ile Gly Gly Val Lys Gly Asn Pro Gly Pro Glu Thr Ile Ser Ser Trp
145                 150                 155                 160

Phe Lys Ile Glu Glu Phe Cys Gly Ser Gly Phe Tyr Lys Leu Val Phe
                165                 170                 175

Cys Pro Thr Val Cys Gly Ser Cys Lys Val Lys Cys Gly Asp Val Gly
            180                 185                 190

Ile Tyr Ile Asp Gln Lys Gly Arg Arg Arg Leu Ala Leu Ser Asp Lys
        195                 200                 205

Pro Phe Ala Phe Glu Phe Asn Lys Thr Val Tyr Phe
    210                 215                 220
```

<210> SEQ ID NO 7
<211> LENGTH: 158
<212> TYPE: PRT
<213> ORGANISM: Molineria latifolia
<220> FEATURE:
<221> NAME/KEY: MISC_FEATURE
<223> OTHER INFORMATION: Curculin-1 GenBank Entry No. P19667

<400> SEQUENCE: 7

```
Met Ala Ala Lys Phe Leu Leu Thr Ile Leu Val Thr Phe Ala Ala Val
 1               5                  10                  15

Ala Ser Leu Gly Met Ala Asp Asn Val Leu Leu Ser Gly Gln Thr Leu
                 20                  25                  30
```

```
His Ala Asp His Ser Leu Gln Ala Gly Ala Tyr Thr Leu Thr Ile Gln
            35                  40                  45

Asn Lys Cys Asn Leu Val Lys Tyr Gln Asn Gly Arg Gln Ile Trp Ala
         50                  55                  60

Ser Asn Thr Asp Arg Arg Gly Ser Gly Cys Arg Leu Thr Leu Leu Ser
 65                  70                  75                  80

Asp Gly Asn Leu Val Ile Tyr Asp His Asn Asn Asp Val Trp Gly
                 85                  90                  95

Ser Ala Cys Trp Gly Asp Asn Gly Lys Tyr Ala Leu Val Leu Gln Lys
                100                 105                 110

Asp Gly Arg Phe Val Ile Tyr Gly Pro Val Leu Trp Ser Leu Gly Pro
             115                 120                 125

Asn Gly Cys Arg Arg Val Asn Gly Gly Ile Thr Val Ala Lys Asp Ser
         130                 135                 140

Thr Glu Pro Gln His Glu Asp Ile Lys Met Val Ile Asn Asn
145                 150                 155

<210> SEQ ID NO 8
<211> LENGTH: 158
<212> TYPE: PRT
<213> ORGANISM: Molineria latifolia
<220> FEATURE:
<221> NAME/KEY: MISC_FEATURE
<223> OTHER INFORMATION: Curculin-2 GenBank Entry No. Q6F495

<400> SEQUENCE: 8

Met Ala Ala Lys Phe Leu Leu Thr Ile Leu Val Thr Phe Ala Ala Val
 1               5                  10                  15

Ala Ser Leu Gly Met Ala Asp Ser Val Leu Leu Ser Gly Gln Thr Leu
             20                  25                  30

Tyr Ala Gly His Ser Leu Thr Ser Gly Ser Tyr Thr Leu Thr Ile Gln
            35                  40                  45

Asn Asn Cys Asn Leu Val Lys Tyr Gln His Gly Arg Gln Ile Trp Ala
         50                  55                  60

Ser Asp Thr Asp Gly Gln Gly Ser Gln Cys Arg Leu Thr Leu Arg Ser
 65                  70                  75                  80

Asp Gly Asn Leu Ile Ile Tyr Asp Asp Asn Asn Met Val Val Trp Gly
                 85                  90                  95

Ser Asp Cys Trp Gly Asn Asn Gly Thr Tyr Ala Leu Val Leu Gln Gln
                100                 105                 110

Asp Gly Leu Phe Val Ile Tyr Gly Pro Val Leu Trp Pro Leu Gly Leu
             115                 120                 125

Asn Gly Cys Arg Ser Leu Asn Gly Glu Ile Thr Val Ala Lys Asp Ser
         130                 135                 140

Thr Glu Pro Gln His Glu Asp Ile Lys Met Val Ile Asn Asn
145                 150                 155

<210> SEQ ID NO 9
<211> LENGTH: 54
<212> TYPE: PRT
<213> ORGANISM: Pentadiplandra brazzeana
<220> FEATURE:
<221> NAME/KEY: MISC_FEATURE
<223> OTHER INFORMATION: Brazzein or Defensin-like protein GenBank Entry
      No. P56552
```

-continued

```
<400> SEQUENCE: 9

Gln Asp Lys Cys Lys Lys Val Tyr Glu Asn Tyr Pro Val Ser Lys Cys
1               5                   10                  15

Gln Leu Ala Asn Gln Cys Asn Tyr Asp Cys Lys Leu Asp Lys His Ala
            20                  25                  30

Arg Ser Gly Glu Cys Phe Tyr Asp Glu Lys Arg Asn Leu Gln Cys Ile
        35                  40                  45

Cys Asp Tyr Cys Glu Tyr
        50

<210> SEQ ID NO 10
<211> LENGTH: 104
<212> TYPE: PRT
<213> ORGANISM: Capparis masaikai
<220> FEATURE:
<221> NAME/KEY: MISC_FEATURE
<223> OTHER INFORMATION: Sweet protein mabinlin-1 GenBank Entry No.
      P80351

<400> SEQUENCE: 10

Glu Pro Leu Cys Arg Arg Gln Phe Gln Gln His Gln His Leu Arg Ala
1               5                   10                  15

Cys Gln Arg Tyr Ile Arg Arg Ala Gln Arg Gly Gly Leu Val Asp
            20                  25                  30

Glu Gln Arg Gly Pro Ala Leu Arg Leu Cys Cys Asn Gln Leu Arg Gln
        35                  40                  45

Val Asn Lys Pro Cys Val Cys Pro Val Leu Arg Gln Ala Ala His Gln
    50                  55                  60

Gln Leu Tyr Gln Gly Gln Ile Glu Gly Pro Arg Gln Val Arg Gln Leu
65                  70                  75                  80

Phe Arg Ala Ala Arg Asn Leu Pro Asn Ile Cys Lys Ile Pro Ala Val
                85                  90                  95

Gly Arg Cys Gln Phe Thr Arg Trp
            100

<210> SEQ ID NO 11
<211> LENGTH: 155
<212> TYPE: PRT
<213> ORGANISM: Capparis masaikai
<220> FEATURE:
<221> NAME/KEY: MISC_FEATURE
<223> OTHER INFORMATION: Sweet protein mabinlin-2 GenBank Entry No.
      P30233

<400> SEQUENCE: 11

Met Ala Lys Leu Ile Phe Leu Phe Ala Thr Leu Ala Leu Phe Val Leu
1               5                   10                  15

Leu Ala Asn Ala Ser Ile Gln Thr Thr Val Ile Glu Val Asp Glu Glu
            20                  25                  30

Glu Asp Asn Gln Leu Trp Arg Cys Gln Arg Gln Phe Leu Gln His Gln
        35                  40                  45

Arg Leu Arg Ala Cys Gln Arg Phe Ile His Arg Arg Ala Gln Phe Gly
    50                  55                  60

Gly Gln Pro Asp Glu Leu Glu Asp Glu Val Glu Asp Asp Asn Asp Asp
65                  70                  75                  80

Glu Asn Gln Pro Arg Arg Pro Ala Leu Arg Gln Cys Cys Asn Gln Leu
                85                  90                  95

Arg Gln Val Asp Arg Pro Cys Val Cys Pro Val Leu Arg Gln Ala Ala
            100                 105                 110
```

```
Gln Gln Val Leu Gln Arg Gln Ile Ile Gln Gly Pro Gln Gln Leu Arg
        115                 120                 125

Arg Leu Phe Asp Ala Ala Arg Asn Leu Pro Asn Ile Cys Asn Ile Pro
130                 135                 140

Asn Ile Gly Ala Cys Pro Phe Arg Ala Trp Pro
145                 150                 155

<210> SEQ ID NO 12
<211> LENGTH: 104
<212> TYPE: PRT
<213> ORGANISM: Capparis masaikai
<220> FEATURE:
<221> NAME/KEY: MISC_FEATURE
<223> OTHER INFORMATION: Sweet protein mabinlin-3 GenBank Entry No.
      P80352

<400> SEQUENCE: 12

Glu Pro Leu Cys Arg Arg Gln Phe Gln Gln His Gln His Leu Arg Ala
1               5                   10                  15

Cys Gln Arg Tyr Leu Arg Arg Arg Ala Gln Arg Gly Gly Leu Ala Asp
            20                  25                  30

Glu Gln Arg Gly Pro Ala Leu Arg Leu Cys Cys Asn Gln Leu Arg Gln
        35                  40                  45

Val Asn Lys Pro Cys Val Cys Pro Val Leu Arg Gln Ala Ala His Gln
    50                  55                  60

Gln Leu Tyr Gln Gly Gln Ile Glu Gly Pro Arg Gln Val Arg Arg Leu
65                  70                  75                  80

Phe Arg Ala Ala Arg Asn Leu Pro Asn Ile Cys Lys Ile Pro Ala Val
                85                  90                  95

Gly Arg Cys Gln Phe Thr Arg Trp
            100

<210> SEQ ID NO 13
<211> LENGTH: 100
<212> TYPE: PRT
<213> ORGANISM: Capparis masaikai
<220> FEATURE:
<221> NAME/KEY: MISC_FEATURE
<223> OTHER INFORMATION: Sweet protein mabinlin-4 GenBank Entry No.
      P80353

<400> SEQUENCE: 13

Glu Pro Leu Cys Arg Arg Gln Phe Gln Gln His Gln His Leu Arg Ala
1               5                   10                  15

Cys Gln Arg Tyr Leu Arg Arg Arg Ala Gln Arg Gly Glu Gln Arg Gly
            20                  25                  30

Pro Ala Leu Arg Leu Cys Cys Asn Gln Leu Arg Gln Val Asn Lys Pro
        35                  40                  45

Cys Val Cys Pro Val Leu Arg Gln Ala Ala His Gln Gln Leu Tyr Gln
    50                  55                  60

Gly Gln Ile Glu Gly Pro Arg Gln Val Arg Arg Leu Phe Arg Ala Ala
65                  70                  75                  80

Arg Asn Leu Pro Asn Ile Cys Lys Ile Pro Ala Val Gly Arg Cys Gln
                85                  90                  95

Phe Thr Arg Trp
            100
```

<210> SEQ ID NO 14
<211> LENGTH: 258
<212> TYPE: PRT
<213> ORGANISM: Ricinus communis
<220> FEATURE:
<221> NAME/KEY: MISC_FEATURE
<223> OTHER INFORMATION: Sweet protein mabinlin-1 chain A GenBank Entry
No. B9SA35

<400> SEQUENCE: 14

```
Met Ala Lys Leu Ile Pro Thr Ile Ala Leu Val Ser Val Leu Leu Phe
1               5                   10                  15

Ile Ile Ala Asn Ala Ser Phe Ala Tyr Arg Thr Thr Ile Thr Thr Ile
            20                  25                  30

Glu Ile Asp Glu Ser Lys Gly Glu Arg Glu Gly Ser Ser Ser Gln Gln
        35                  40                  45

Cys Arg Gln Glu Val Gln Arg Lys Asp Leu Ser Ser Cys Glu Arg Tyr
    50                  55                  60

Leu Arg Gln Ser Ser Ser Arg Arg Ser Pro Gly Glu Glu Val Leu Arg
65                  70                  75                  80

Met Pro Gly Asp Glu Asn Gln Gln Gln Glu Ser Gln Gln Leu Gln Gln
                85                  90                  95

Cys Cys Asn Gln Val Lys Gln Val Arg Asp Glu Cys Gln Cys Glu Ala
            100                 105                 110

Ile Lys Tyr Ile Ala Glu Asp Gln Ile Gln Gln Gly Gln Leu His Gly
        115                 120                 125

Glu Glu Ser Glu Arg Val Ala Gln Arg Ala Gly Glu Ile Val Ser Ser
    130                 135                 140

Cys Gly Val Arg Cys Met Arg Gln Thr Arg Thr Asn Pro Ser Gln Gln
145                 150                 155                 160

Gly Cys Arg Gly Gln Ile Gln Glu Gln Gln Asn Leu Arg Gln Cys Gln
                165                 170                 175

Glu Tyr Ile Lys Gln Gln Val Ser Gly Gln Gly Pro Arg Arg Ser Asp
            180                 185                 190

Asn Gln Glu Arg Ser Leu Arg Gly Cys Cys Asp His Leu Lys Gln Met
        195                 200                 205

Gln Ser Gln Cys Arg Cys Glu Gly Leu Arg Gln Ala Ile Glu Gln Gln
    210                 215                 220

Gln Ser Gln Gly Gln Leu Gln Gly Gln Asp Val Phe Glu Ala Phe Arg
225                 230                 235                 240

Thr Ala Ala Asn Leu Pro Ser Met Cys Gly Val Ser Pro Thr Glu Cys
                245                 250                 255

Arg Phe
```

<210> SEQ ID NO 15
<211> LENGTH: 96
<212> TYPE: PRT
<213> ORGANISM: Artificial Sequence
<220> FEATURE:
<223> OTHER INFORMATION: DM3

<400> SEQUENCE: 15

```
Gly Asn Trp Glu Ile Ile Asp Thr Gly Pro Phe Thr Gln Lys Leu Gly
1               5                   10                  15

Lys Phe Ala Val Asp Glu Ala Asn Lys Ile Gly Lys Tyr Gly Thr Leu
            20                  25                  30

Thr Phe Thr Lys Val Ile Arg Pro Thr Met Lys Lys Thr Ile Tyr Glu
        35                  40                  45
```

```
Asn Glu Gly Phe Arg Glu Ile Lys Gly Tyr Glu Tyr Gln Leu Tyr Val
 50                  55                  60

Lys Ala Asn Asp Lys Leu Phe Arg Ala Asp Ile Ser Glu Asp Tyr Lys
 65                  70                  75                  80

Thr Arg Gly Leu Lys Leu Leu Arg Phe Asn Gly Pro Val Pro Pro Pro
                 85                  90                  95
```

<210> SEQ ID NO 16
<211> LENGTH: 96
<212> TYPE: PRT
<213> ORGANISM: Artificial Sequence
<220> FEATURE:
<223> OTHER INFORMATION: DM8

<400> SEQUENCE: 16

```
Gly Asn Trp Glu Ile Ile Asp Ile Gly Pro Phe Thr Gln Asn Leu Gly
 1               5                  10                  15

Lys Phe Ala Val Asp Glu Val Asn Lys Ile Gly Gln Tyr Gly Arg Leu
                 20                  25                  30

Thr Phe Asn Lys Val Ile Arg Pro Cys Met Lys Lys Thr Ile Tyr Glu
             35                  40                  45

Asn Glu Gly Phe Arg Glu Ile Lys Gly Tyr Glu Tyr Gln Leu Tyr Val
 50                  55                  60

Lys Ala Ser Asp Lys Leu Phe Arg Ala Asp Ile Ser Glu Asp Tyr Lys
 65                  70                  75                  80

Thr Arg Gly Arg Lys Leu Leu Arg Phe Asn Gly Pro Val Pro Pro Pro
                 85                  90                  95
```

<210> SEQ ID NO 17
<211> LENGTH: 96
<212> TYPE: PRT
<213> ORGANISM: Artificial Sequence
<220> FEATURE:
<223> OTHER INFORMATION: DM9

<400> SEQUENCE: 17

```
Gly Asn Trp Glu Ile Ile Asp Ile Gly Pro Phe Thr Gln Asn Leu Gly
 1               5                  10                  15

Lys Phe Ala Val Asp Glu Ala Asn Lys Ile Gly Gln Tyr Gly Arg Leu
                 20                  25                  30

Thr Phe Asn Lys Val Ile Arg Pro Cys Met Lys Lys Thr Ile Tyr Glu
             35                  40                  45

Asn Glu Gly Phe Arg Glu Ile Lys Gly Tyr Glu Tyr Gln Leu Tyr Val
 50                  55                  60

Arg Ala Ser Asp Lys Leu Phe Arg Ala Asp Ile Ser Glu Asp Tyr Lys
 65                  70                  75                  80

Thr Arg Gly Arg Lys Leu Leu Arg Phe Asn Gly Pro Val Pro Pro Pro
                 85                  90                  95
```

<210> SEQ ID NO 18
<211> LENGTH: 96
<212> TYPE: PRT
<213> ORGANISM: Artificial Sequence
<220> FEATURE:
<223> OTHER INFORMATION: DM10

```
<400> SEQUENCE: 18

Gly Glu Trp Glu Ile Ile Asp Ile Gly Pro Phe Thr Gln Asn Leu Gly
1               5                   10                  15

Lys Phe Ala Val Asp Glu Glu Asn Lys Ile Gly Lys Tyr Gly Thr Leu
            20                  25                  30

Thr Phe Thr Lys Val Ile Arg Pro Cys Met Lys Lys Thr Ile Tyr Glu
        35                  40                  45

Asn Glu Gly Phe Arg Glu Ile Lys Gly Tyr Glu Tyr Gln Leu Tyr Val
    50                  55                  60

Tyr Ala Asn Asp Lys Leu Phe Arg Ala Asp Ile Ser Glu Asp Tyr Lys
65                  70                  75                  80

Thr Arg Gly Arg Lys Leu Leu Arg Phe Asn Gly Pro Val Pro Pro Pro
                85                  90                  95

<210> SEQ ID NO 19
<211> LENGTH: 96
<212> TYPE: PRT
<213> ORGANISM: Artificial Sequence
<220> FEATURE:
<223> OTHER INFORMATION: DM11

<400> SEQUENCE: 19

Gly Glu Trp Glu Ile Ile Asp Thr Gly Pro Phe Thr Gln Lys Leu Gly
1               5                   10                  15

Lys Phe Ala Val Asp Glu Glu Asn Lys Ile Gly Gln Tyr Gly Arg Leu
            20                  25                  30

Thr Phe Asn Lys Val Ile Arg Pro Thr Met Lys Lys Thr Ile Tyr Glu
        35                  40                  45

Asn Glu Gly Phe Arg Glu Ile Lys Gly Tyr Glu Tyr Gln Leu Tyr Val
    50                  55                  60

Tyr Ala Ser Asp Lys Leu Phe Arg Ala Asp Ile Ser Glu Asp Tyr Lys
65                  70                  75                  80

Thr Arg Gly Leu Lys Leu Leu Arg Phe Asn Gly Pro Val Pro Pro Pro
                85                  90                  95

<210> SEQ ID NO 20
<211> LENGTH: 96
<212> TYPE: PRT
<213> ORGANISM: Artificial Sequence
<220> FEATURE:
<223> OTHER INFORMATION: DM12

<400> SEQUENCE: 20

Gly Glu Trp Glu Ile Ile Asp Thr Gly Pro Phe Thr Gln Asn Leu Gly
1               5                   10                  15

Lys Phe Ala Val Asp Glu Glu Asn Lys Ile Gly Gln Tyr Gly Arg Leu
            20                  25                  30

Thr Phe Asn Lys Val Ile Arg Pro Thr Met Lys Lys Thr Ile Tyr Glu
        35                  40                  45

Asn Glu Gly Phe Arg Glu Ile Lys Gly Tyr Glu Tyr Gln Leu Tyr Val
    50                  55                  60

Tyr Ala Ser Asp Lys Leu Phe Arg Ala Asp Ile Ser Glu Asp Tyr Lys
65                  70                  75                  80

Thr Arg Gly Leu Lys Leu Leu Arg Phe Asn Gly Pro Val Pro Pro Pro
                85                  90                  95
```

<210> SEQ ID NO 21
<211> LENGTH: 207
<212> TYPE: PRT
<213> ORGANISM: Artificial Sequence
<220> FEATURE:
<223> OTHER INFORMATION: TM1

<400> SEQUENCE: 21

```
Ala Thr Phe Asp Ile Arg Asn Asn Cys Pro Tyr Thr Val Trp Ala Ala
1               5                   10                  15

Ala Ser Lys Gly Asp Ala Ala Leu Asp Ala Gly Arg Arg Leu Asp
            20                  25                  30

Arg Gly Gln Ser Trp Thr Ile Asn Val Glu Pro Gly Thr Asn Gly Gly
        35                  40                  45

Lys Ile Trp Ala Arg Thr Asn Cys Tyr Phe Asp Asp Ser Gly Ser Gly
    50                  55                  60

Ile Cys Lys Thr Gly Asp Cys Gly Gly Leu Leu Arg Cys Lys Arg Phe
65                  70                  75                  80

Gly Arg Pro Pro Thr Thr Leu Ala Glu Phe Ser Leu Asn Gln Tyr Gly
                85                  90                  95

Lys Asp Tyr Phe Asp Ile Ser Leu Ile Lys Gly Phe Asn Val Pro Met
            100                 105                 110

Glu Phe Ser Pro Thr Ser Arg Gly Cys Arg Gly Ile Arg Cys Thr Ala
        115                 120                 125

Asp Ile Asn Gly Gln Cys Pro Asn Glu Leu Arg Ala Pro Gly Gly Gly
    130                 135                 140

Cys Asn Asp Ala Cys Thr Val Phe Gln Thr Ser Glu Tyr Cys Cys Thr
145                 150                 155                 160

Thr Gly Lys Cys Gly Pro Thr Glu Tyr Ser Arg Phe Phe Lys Asp Arg
                165                 170                 175

Cys Pro Asp Ala Phe Ser Tyr Val Leu Asp Asp Pro Thr Thr Val Thr
            180                 185                 190

Cys Pro Gly Ser Ser Asn Tyr Arg Val Thr Phe Cys Pro Thr Ala
        195                 200                 205
```

<210> SEQ ID NO 22
<211> LENGTH: 627
<212> TYPE: DNA
<213> ORGANISM: Artificial Sequence
<220> FEATURE:
<223> OTHER INFORMATION: TD1

<400> SEQUENCE: 22

```
gcaacctttg atatcagaaa taactgtccc tacacagtat gggctgctgc atctaaaggt      60
gatgctgcac ttgacgccgg tggcagacgt ctagatcgtg acagtcctg gaccatcaat      120 gttgagcctg gtacaaatgg tggaaagatt tgggctagga ctaattgcta ctttgatgac      180
tctggatccg gtatatgtaa gactggtgac tgtggcggat tgttgagatg taagagattc      240
ggtaggcccc caactacact ggctgaattc tcgttgaatc aatatggtaa agattacttt      300
gacattagtc tgattaaggg attcaacgtt cctatggaat tctccccaac ctcacgtggg      360
tgcagaggaa tcagatgtac ggctgacatc aacggtcaat gtccgaatga attgcgagcc      420
cctggtggtg gatgtaacga tgcatgcaca gtgttccaaa cttctgagta ttgttgtact      480
actggtaagt gcggaccaac tgagtactcc agatttttca agatcgttg tccagatgca      540 ttcagctatg tgttagacga cccaactaca gttcgtgcc caggttcaag caattacaga      600
gtcaccttct gtcctacagc ttaatag                                         627
```

<210> SEQ ID NO 23
<211> LENGTH: 207
<212> TYPE: PRT
<213> ORGANISM: Artificial Sequence
<220> FEATURE:
<223> OTHER INFORMATION: TM2

<400> SEQUENCE: 23

```
Ala Thr Phe Asp Ile Arg Asn Asn Cys Pro Tyr Thr Val Trp Ala Ala
1               5                   10                  15

Ala Ser Lys Gly Asp Ala Ala Leu Asp Ala Gly Arg Arg Leu Asp
            20                  25                  30

Arg Gly Gln Ser Trp Thr Ile Asn Val Glu Pro Gly Thr Asn Gly Gly
        35                  40                  45

Lys Ile Trp Ala Arg Thr Asn Cys Tyr Phe Asp Asp Ser Gly Ser Gly
    50                  55                  60

Ile Cys Lys Thr Gly Asp Cys Gly Gly Leu Leu Arg Cys Lys Arg Phe
65                  70                  75                  80

Gly Arg Pro Pro Thr Thr Leu Ala Glu Phe Ser Leu Asn Gln Tyr Gly
                85                  90                  95

Lys Asp Tyr Ile Asp Ile Ser Asn Ile Lys Gly Phe Asn Val Pro Met
            100                 105                 110

Glu Phe Ser Pro Thr Ser Arg Gly Cys Arg Gly Val Arg Cys Thr Ala
        115                 120                 125

Asp Ile Asn Gly Gln Cys Pro Asn Glu Leu Arg Ala Pro Gly Gly Gly
    130                 135                 140

Cys Asn Asp Ala Cys Thr Val Phe Gln Thr Ser Glu Tyr Cys Cys Thr
145                 150                 155                 160

Thr Gly Lys Cys Gly Pro Thr Glu Tyr Ser Arg Phe Phe Lys Asp Arg
                165                 170                 175

Cys Pro Asp Ala Phe Ser Tyr Val Leu Asp Asp Pro Thr Thr Val Thr
            180                 185                 190

Cys Pro Gly Ser Ser Asn Tyr Arg Val Thr Phe Cys Pro Thr Ala
        195                 200                 205
```

<210> SEQ ID NO 24
<211> LENGTH: 627
<212> TYPE: DNA
<213> ORGANISM: Artificial Sequence
<220> FEATURE:
<223> OTHER INFORMATION: TD2

<400> SEQUENCE: 24

```
gcaacctttg atatcagaaa taactgtccc tacacagtat gggctgctgc atctaaaggt      60
gatgctgcac ttgacgccgg tggcagacgt ctagatcgtg acagtcctg gaccatcaat     120 gttgagcctg gtacaaatgg tggaaagatt tgggctagga ctaattgcta ctttgatgac    180
tctggatccg gtatatgtaa gactggtgac tgtggcggat tgttgagatg taagagattc    240
ggtaggcccc caactacact ggctgaattc tcgttgaatc aatatggtaa agattacatc    300
gacattagta acattaaggg attcaacgtt cctatggaat tctccccaac ctcacgtggg    360
tgcagaggag tcagatgtac ggctgacatc aacggtcaat gtccgaatga attgcgagcc    420
cctggtggtg gatgtaacga tgcatgcaca gtgttccaaa cttctgagta ttgttgtact    480
actggtaagt gcggaccaac tgagtactcc agatttttca agatcgttg tccagatgca     540 ttcagctatg tgttagacga cccaactaca gttcgtgcc caggttcaag caattacaga     600
gtcaccttct gtcctacagc ttaatag                                         627
```

<210> SEQ ID NO 25
<211> LENGTH: 207
<212> TYPE: PRT
<213> ORGANISM: Artificial Sequence
<220> FEATURE:
<223> OTHER INFORMATION: TM3

<400> SEQUENCE: 25

```
Ala Thr Phe Glu Ile Val Asn Arg Cys Ser Tyr Thr Val Trp Ala Ala
1               5                   10                  15

Ala Ser Lys Gly Asp Ala Ala Leu Asp Ala Gly Arg Gln Leu Asn
            20                  25                  30

Ser Gly Glu Ser Trp Thr Ile Asn Val Glu Pro Gly Thr Asn Gly Gly
        35                  40                  45

Lys Ile Trp Ala Arg Thr Asp Cys Tyr Phe Asp Asp Ser Gly Ser Gly
    50                  55                  60

Ile Cys Lys Thr Gly Asp Cys Gly Gly Leu Leu Arg Cys Lys Arg Phe
65                  70                  75                  80

Gly Arg Pro Pro Thr Thr Leu Ala Glu Phe Ser Leu Asn Gln Tyr Gly
                85                  90                  95

Lys Asp Tyr Phe Asp Ile Ser Leu Ile Lys Gly Phe Asn Val Pro Met
            100                 105                 110

Asn Phe Ser Pro Thr Thr Arg Gly Cys Arg Gly Ile Arg Cys Ala Ala
        115                 120                 125

Asp Ile Val Gly Gln Cys Pro Ala Lys Leu Lys Ala Pro Gly Gly Gly
    130                 135                 140

Cys Asn Asp Ala Cys Thr Val Phe Gln Thr Ser Glu Tyr Cys Cys Thr
145                 150                 155                 160

Thr Gly Lys Cys Gly Pro Thr Glu Tyr Ser Arg Phe Phe Lys Arg Leu
                165                 170                 175

Cys Pro Asp Ala Phe Ser Tyr Val Leu Asp Lys Pro Thr Thr Val Thr
            180                 185                 190

Cys Pro Gly Ser Ser Asn Tyr Arg Val Thr Phe Cys Pro Thr Ala
        195                 200                 205
```

<210> SEQ ID NO 26
<211> LENGTH: 627
<212> TYPE: DNA
<213> ORGANISM: Artificial Sequence
<220> FEATURE:
<223> OTHER INFORMATION: TD3

<400> SEQUENCE: 26

```
gccacatttg aaatagtcaa tcgttgttcc tatactgttt gggctgctgc atcaaagggt    60
gatgcagctc tagatgccgg tggcagacaa cttaatagcg gtgagtcctg gacaatcaat   120
gttgagcccg gaactaacgg tggaaaaatc tgggctagga ctgactgtta ctttgacgac   180
tctggttccg gaatctgcaa aacgggtgat tgtggtggac tgttacgttg taaaagattc   240
ggtaggccac caactacctt ggcagaattt cccctgaatc agtacggtaa agattatttc   300
gatatttcgt tgattaaggg tttcaatgtg cctatgaact tttctcctac taccagaggt   360
tgcagaggaa tcagatgtgc tgctgatatt gtgggacaat gtccggcaaa gttgaaagct   420
cctggtggcg ggtgtaacga cgcttgcaca gtctttcaaa caagcgagta ctgttgtaca   480
actggtaagt gcggtccaac agaatatagt cgtttcttta agagactttg tcctgacgca   540
ttctcttatg tattggacaa accaactaca gttacgtgcc caggatcatc aaactacaga   600
gttactttct gtccaaccgc ctaatag                                       627
```

```
<210> SEQ ID NO 27
<211> LENGTH: 207
<212> TYPE: PRT
<213> ORGANISM: Artificial Sequence
<220> FEATURE:
<223> OTHER INFORMATION: TM4

<400> SEQUENCE: 27

Ser Thr Trp Glu Ile Val Asn Asn Cys Pro Tyr Thr Val Trp Ala Ala
1               5                   10                  15

Ala Ser Lys Gly Asp Ala Ala Leu Asp Ala Gly Gly Arg Gln Leu Pro
            20                  25                  30

Pro Gly Glu Ser Trp Thr Ile Asn Val Glu Pro Gly Thr Asn Gly Gly
        35                  40                  45

Lys Ile Trp Ala Arg Thr Asp Cys Tyr Phe Asp Asp Ser Gly Ser Gly
50                  55                  60

Ile Cys Lys Thr Gly Asp Cys Gly Gly Leu Leu Arg Cys Lys Arg Phe
65                  70                  75                  80

Gly Arg Pro Pro Thr Thr Leu Ala Glu Phe Ser Leu Asn Gln Tyr Gly
                85                  90                  95

Lys Asp Tyr Ile Asp Ile Ser Leu Ile Lys Gly Phe Asn Val Pro Ile
            100                 105                 110

Glu Val Gln Pro Thr Thr Thr Gly Cys Arg Gly Val Arg Cys Ser Ser
        115                 120                 125

Pro Ile Gln Thr Gln Cys Pro Ala Lys Leu Arg His Pro Gly Gly Gly
130                 135                 140

Cys Asn Asp Pro Cys Thr Val Tyr Gln Thr Ser Glu Tyr Cys Cys Thr
145                 150                 155                 160

Thr Gly Lys Cys Gly Pro Thr Glu Tyr Ser Arg Tyr Phe Lys Arg Leu
                165                 170                 175

Cys Pro Glu Ala Phe Ser Tyr Val Leu Asp Lys Pro Thr Thr Val Thr
            180                 185                 190

Cys Pro Gly Ser Ser Arg Tyr Arg Val Thr Phe Cys Pro Thr Thr
        195                 200                 205

<210> SEQ ID NO 28
<211> LENGTH: 627
<212> TYPE: DNA
<213> ORGANISM: Artificial Sequence
<220> FEATURE:
<223> OTHER INFORMATION: TD4

<400> SEQUENCE: 28
tctacttggg aaattgttaa caactgtcca tacaccgtgt gggctgctgc tagtaagggt      60
gatgctgctt tggacgccgg tggtcgtcaa ctaccacctg gcgagtcctg gactatcaat     120
gttgaaccgg gaacaaatgg tggtaaaatc tgggccagaa cagactgtta tttcgatgat     180
tctggatccg gtatttgtaa gactggtgac tgtggtggat tgctgaggtg taaaagattt     240
ggtcgtcctc caactacgtt agcagagttt tcattgaatc aatacggtaa agactacatt     300
gatatttcat tgataaaggg atttaacgtc cctatcgaag tacagccaac tacgacaggt     360
tgcagaggag ttagatgttc cagcccaatc cagactcaat gtccagcaaa gcttagacat     420
cccggtggtg ggtgtaatga cccatgcact gtgtaccaaa catctgagta ctgttgtacc     480
accggaaagt gcggccctac tgaatattcc aggtatttca aaagattgtg ccccgaggca     540
ttcagttacg tcctggataa acctacaaca gttacttgtc ctggatcgtc aagatatcgt     600
gtgacattct gtccaactac ataatag                                         627
```

<210> SEQ ID NO 29
<211> LENGTH: 207
<212> TYPE: PRT
<213> ORGANISM: Artificial Sequence
<220> FEATURE:
<223> OTHER INFORMATION: TM5

<400> SEQUENCE: 29

```
Ala Thr Trp Glu Ile Val Asn Arg Cys Ser Tyr Thr Val Trp Ala Ala
1               5                   10                  15

Ala Ser Lys Gly Asp Ala Ala Leu Asp Ala Gly Arg Gln Leu Asn
            20                  25                  30

Ser Gly Glu Ser Trp Thr Ile Asn Val Glu Pro Gly Thr Asn Gly Gly
        35                  40                  45

Lys Ile Trp Ala Arg Thr Asp Cys Tyr Phe Asp Asp Ser Gly Ser Gly
    50                  55                  60

Ile Cys Lys Thr Gly Asp Cys Gly Gly Leu Leu Arg Cys Lys Arg Phe
65              70                  75                  80

Gly Arg Pro Pro Thr Thr Leu Ala Glu Phe Ser Leu Asn Gln Tyr Gly
                85                  90                  95

Lys Asp Tyr Ile Asp Ile Ser Leu Ile Lys Gly Phe Asn Val Pro Ile
            100                 105                 110

Asn Val Ser Pro Thr Thr Arg Gly Cys Arg Gly Val Arg Cys Ala Ala
        115                 120                 125

Asp Ile Val Gly Gln Cys Pro Ala Lys Leu Lys Ala Pro Gly Gly Gly
    130                 135                 140

Cys Asn Asp Pro Cys Thr Val Phe Gln Thr Ser Glu Tyr Cys Cys Thr
145                 150                 155                 160

Thr Gly Lys Cys Gly Pro Thr Glu Tyr Ser Arg Phe Phe Lys Arg Leu
                165                 170                 175

Cys Pro Asp Ala Phe Ser Tyr Val Leu Asp Lys Pro Thr Thr Val Thr
            180                 185                 190

Cys Pro Gly Ser Ser Asn Tyr Arg Val Thr Phe Cys Pro Thr Ala
        195                 200                 205
```

<210> SEQ ID NO 30
<211> LENGTH: 627
<212> TYPE: DNA
<213> ORGANISM: Artificial Sequence
<220> FEATURE:
<223> OTHER INFORMATION: TD5

<400> SEQUENCE: 30

```
gctacgtggg aaattgtgaa tagatgttct tatacagtgt gggcagccgc aagtaaaggt    60
gacgctgctc tggatgccgg tggtagacaa ctgaactccg gcgaatcttg gactataaat   120
gtcgagccag gaaccaatgg tgggaaaatc tgggctagaa cagattgtta tttcgacgac   180
tccggttccg gtatttgtaa gactggtgac tgccgtggat tattgcgttg caaaagattt   240
ggaaggcctc caactacact agcagagttt agcttgaatc agtacggaaa agattatatc   300
gatatttcac tcatcaaggg tttcaacgtt cctatcaatg tttcaccaac cacccgtggt   360
tgtaggggtg ttagatgtgc agccgatatt gtaggacaat gtccagctaa gcttaaggca   420
ccgggtggtg gatgtaacga tccttgcaca gtgtttcaaa catctgagta ctgttgcact   480
actggaaagt gtggtcccac tgaatattca cgtttcttca aaagattgtg tccagacgct   540
ttctcgtacg ttttggacaa accaacgact gttacatgtc ccggcagttc aactacaga   600 gtcactttt gccctacagc ttaatag                                        627
```

<210> SEQ ID NO 31
<211> LENGTH: 207
<212> TYPE: PRT
<213> ORGANISM: Artificial Sequence
<220> FEATURE:
<223> OTHER INFORMATION: TM6

<400> SEQUENCE: 31

```
Ser Thr Phe Glu Ile Val Asn Asn Cys Pro Tyr Thr Val Trp Ala Ala
1               5                   10                  15

Ala Ser Lys Gly Asp Ala Ala Leu Asp Ala Gly Gly Arg Gln Leu Pro
                20                  25                  30

Pro Gly Glu Ser Trp Thr Ile Asn Val Glu Pro Gly Thr Asn Gly Gly
            35                  40                  45

Lys Ile Trp Ala Arg Thr Asp Cys Tyr Phe Asp Asp Ser Gly Ser Gly
        50                  55                  60

Ile Cys Lys Thr Gly Asp Cys Gly Gly Leu Leu Arg Cys Lys Arg Phe
65                  70                  75                  80

Gly Arg Pro Pro Thr Thr Leu Ala Glu Phe Ser Leu Asn Gln Tyr Gly
                85                  90                  95

Lys Asp Tyr Ile Asp Ile Ser Asn Ile Lys Gly Phe Asn Val Pro Met
            100                 105                 110

Glu Phe Gln Pro Thr Thr Thr Gly Cys Arg Gly Val Arg Cys Ser Ser
        115                 120                 125

Pro Ile Gln Thr Gln Cys Pro Ala Lys Leu Arg His Pro Gly Gly Gly
    130                 135                 140

Cys Asn Asp Ala Cys Thr Val Tyr Gln Thr Ser Glu Tyr Cys Cys Thr
145                 150                 155                 160

Thr Gly Lys Cys Gly Pro Thr Glu Tyr Ser Arg Tyr Phe Lys Arg Leu
                165                 170                 175

Cys Pro Glu Ala Phe Ser Tyr Val Leu Asp Lys Pro Thr Thr Val Thr
            180                 185                 190

Cys Pro Gly Ser Ser Arg Tyr Arg Val Thr Phe Cys Pro Thr Thr
        195                 200                 205
```

<210> SEQ ID NO 32
<211> LENGTH: 627
<212> TYPE: DNA
<213> ORGANISM: Artificial Sequence
<220> FEATURE:
<223> OTHER INFORMATION: TD6

<400> SEQUENCE: 32

```
tctactttttg aaattgttaa caactgtcca tacaccgtat gggctgctgc tagtaagggt      60
gatgctgctt tggacgccgg tggtcgtcaa ctaccacctg gcgagtcctg gactatcaat     120
gttgaaccgg gaacaaatgg tggtaaaatc tgggccagaa cagactgtta tttcgatgat     180
tctggatccg gtatttgtaa gactggtgac tgtggtggat tgctgaggtg taaaagattt     240
ggtcgtcctc ccactacgtt agcagagttt tcattgaatc aatacggtaa agactacatt     300
gatatttcaa atataaaggg atttaacgtc cctatggaat tcagccaac  tacgacaggt     360 tgcagaggag ttagatgttc agcccaatc  cagactcaat gtccagcaaa gcttagacat     420
cccggtggtg ggtgtaatga cgcatgcact gtgtaccaaa catctgagta ctgttgtacc     480
accggaaagt gcggccctac tgaatattcc aggtatttca aaagattgtg ccccgaggca     540
```

-continued

```
ttcagttacg tcctggataa acctacaaca gttacttgtc ctggatcgtc aagatatcgt        600
gtgacattct gtccaactac ataatag                                            627
```

TASTE AND FLAVOR-MODIFIER PROTEINS

TECHNOLOGICAL FIELD

The present invention relates to taste and flavor proteins.

BACKGROUND ART

References considered to be relevant as background to the presently disclosed subject matter are listed below:
GB2123672
WO8402450
Leone, S. et al. Sweeter and stronger: enhancing sweetness and stability of the single chain monellin MNEI through molecular design. Sci. Rep. 6, 34045; doi: 10.1038/srep34045 (2016)
Masuda, T. et al. A Hypersweet Protein: Removal of The Specific Negative Charge at Asp21 Enhances Thaumatin Sweetness. Sci. Rep. 6, 20255; doi: 10.1038/srep20255 (2016)
Samish I., S, MacDermaid C M., S, Perez-Aguilar J M P., Saven J G. P I, (2011). Theoretical and Computational Protein Design. Annu Rev Phys Chem 62:129-149
Samish I., (Editor), Computational Protein Design (2017), Methods in Molecular Biology, Springer Protocols, Humana Press.
Zhao, Meng & Xu, Xiangqun & Liu, Bo. (2018). Structure basis of the improved sweetness and thermostability of a unique double-sites single-chain sweet-tasting protein monellin (MNEI) mutant. Biochimie. 154;
Zheng W., et al. (2018) Expression, purification and characterization of a novel double-sites mutant of the single-chain sweet-tasting protein monellin (MNEI) with both improved sweetness and stability. Protein Expr Purif., 143:52-56.
Pica A., et al (2018) pH driven fibrillar aggregation of the super-sweet protein Y65R-MNEI: A step-by-step structural analysis. Biochim Biophys Acta Gen Subj., 1862: 808-815.

BACKGROUND

The sweetening market is dominated by sugar and high fructose syrup with less than 10% of the market share consisting of other sweeteners including artificial sweeteners and sweeteners derived from natural sources e.g. stevia and monk-fruit extract.

GB2123672 describes sweet proteins such as Thaumatin and Monellin and a weakly acidic polysaccharide gum incorporated, optionally together with a food acid or bulking agent, in various beverages, mouth washes or in a pharmaceutical base.

WO8402450 describes application of Thaumatin or Monellin to the surface of a chewing gum composition comprising gum base, sweetener and flavoring.

Leone, S. et al., Zhao et al., Zheng W., et al. and Pica A., et al describe mutants of MNEI.

Masuda, T. et al. describes a hypersweet Thaumatin derivative.

Computational tools for design of proteins have emerged as an alternative reliable method in designing proteins with improved specific features as described in Samish et al (2011) and (2017).

GENERAL DESCRIPTION

In accordance with some aspects, the present disclosure provides a modified protein comprising an amino acid sequence that has one or more amino acids replacements from a reference protein, wherein the modified protein has at least one improved food-related property compared to the reference protein. In accordance with some embodiments, the modified protein comprises at least two amino acids replacements from the reference protein.

In accordance with some aspects, the present disclosure provides a modified protein comprising an amino acid sequence denoted by SEQ ID NO:5, comprising at least three amino acid substitutions at residues E2, E23 and Y65 of SEQ ID NO:5, wherein the modified protein has at least one improved food-related property compared with SEQ ID NO:5.

In accordance with some aspects, the present disclosure provides a food product comprising a modified protein comprising an amino acid sequence that has one or more amino acids replacements from a reference protein, wherein the modified protein has at least one improved food-related property compared to the reference protein. In accordance with some embodiments, the modified protein comprise at least two amino acids replacements from the reference protein.

In accordance with some aspects, the present disclosure provides a food product comprising a modified protein comprising a modified protein comprising an amino acid sequence denoted by SEQ ID NO:5, comprising at least three amino acid substitutions at residues E2, E23 and Y65 of SEQ ID NO:5, wherein the modified protein has at least one improved food-related property compared with SEQ ID NO:5.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
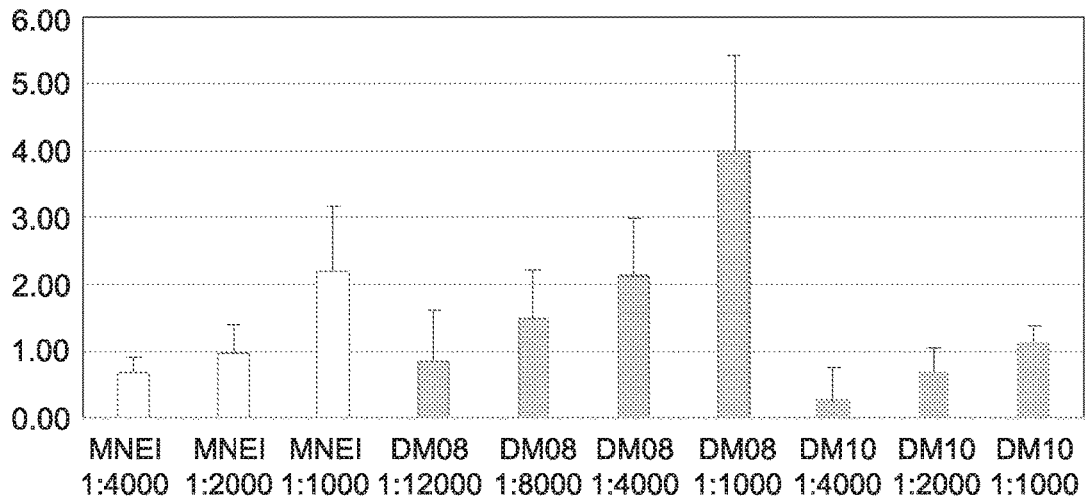
FIG. 1 is a histogram showing sweetness average score of MNEI and MNEI-based modified proteins.

Artificial low calorie sweeteners are available in the market and some are known to have side effects. For example, saccharine has been widely used to sweeten foods and beverages without calories or carbohydrate and it's use was linked with development of bladder cancer. Thus, there is a need for potential replacements of the currently available artificial low calorie sweeteners that will provide on one hand, an optimal sensory profile and on the other hand will be suitable for use in food products and beverages.

The present disclosure relates to novel sweet proteins and novel taste modifying proteins and is based on optimization methods, for example computational methods, resulting in novel proteins that exhibit improved properties relative to known sweeteners.

Surprisingly, the inventors have found that introducing various specific substitutions in an amino acid sequence of a known protein (denoted herein as a "reference protein")

resulted in a novel protein having at least one improved property as compared to the reference protein. It was suggested that the at least one improved property of the novel protein may be of a significant importance in the fitness and utilization of the modified protein in food and beverage applications.

Specifically, as shown in the Examples below, the novel proteins (denoted herein as "modified protein" or "designer protein") exhibited improved sensory profile and/or thermal stability as compared with their reference protein. The sensory profile as described herein relates to a taste profile (e.g. sweetness potency, after taste and lingering).

Thus, the present disclosure in its broadest aspect relates to a modified protein comprising an amino acid sequence that has at least one amino acid replacement (substitution) in an amino acid sequence of a reference protein, wherein the modified protein has at least one improved food-related property as compared with the reference protein.

In some embodiments, the modified protein comprising an amino acid sequence that has at least two amino acids replacements (substitutions), at times three amino acids replacements (substitutions) in an amino acid sequence of a reference protein.

The at least one improved food-related property encompasses a property that enable the fitness of the modified protein in food and beverage applications such as flavor, texture, taste, sweetness threshold, sweetness level, sweetness profile, sensory profile, sweetness kinetics, stability (structural and functional), heat resistance, fitness to food matrix, shelf-life, masking and/or enhancement of other flavor, off-taste, taste onset, lingering taste, roundness of taste or sugar-like taste.

In some embodiments, the at least one food-related property is sensory-affecting property. The term "sensory-affecting property" as used herein refers to a change in the sensory impression as determined, for example, by a sense of taste. The sensory-affecting property include for example sweetness profile such as sweetness potency (sugar-like flavor), sweetness kinetics (onset time, lingering time, taste duration), lack of off-taste, and masking or enhancing of other tastes, off-taste (e.g. metallic taste). For example, an improved property relates with increases sweetness, reduced onset time or reduced lingering taste.

In accordance with some embodiments wherein the at least one property is the sensory-affecting property, the modified protein may be considered as a sugar substitute. In some embodiments, the at least one food-related property is at least one of sweetness potency, reduced onset time or reduced lingering taste.

In some embodiments, the at least one food-related property is stability. In some embodiments, the stability is at least one of thermal stability, longer shelf-life, stability to low-pH, salt concentration stability, ionic strength stability or stability in a fat-containing or protein-containing matrix. In some embodiments, the at least one food-related property is thermal stability.

In some embodiments, the at least one food-related property is increased shelf-life stability. For example, the modified protein may be stable for at least a week, two weeks, a month and even a year.

As detailed above, the modified protein may be used in combination with at least one additional food ingredient. In some embodiments, the at least one food-related property may refer to a synergistic effect between the modified protein and at least one food ingredient. Non-limiting examples of a food ingredient include artificial or natural flavor, food additive, food coloring, preservative or an additional sugar additive. The food ingredient may have a masking taste effect or enhancing taste effect.

As described herein, the reference protein is a taste modifying protein and/or a taste enhancer protein and/or a taste protein and specifically a sweet protein. A taste modifying protein elicit a sweet taste of a non-sweet substance, for example water and sour substances. A tasty protein as used herein is known to bind to taste receptors and evokes a taste sensation. A sweet protein as used herein is known to bind to the sweet receptor and to evoke a sensation of sweetness. Non-limiting examples of a sweet receptor include Taste receptor type 1 member 1 (TAS1R1, Uniprot ID for human gene: TS1R1_HUMAN), Taste receptor type 1 member 2 (TAS1R2, T1R2, TR2, UniProt—Q8TE23), Taste receptor type 1 member 3 (TAS1R3, T1R3, UniProt—Q7RTX0).

The reference protein may vary in length. In some embodiments, the reference protein comprises at least 45 amino acids, at least 80 amino acids, at least 100 amino acids, at least 258 amino acids. In some embodiments, the reference protein has a length of 45 amino acids, 50 amino acids, 54 amino acids, 97 amino acids, 100 amino acids, 158 amino acids, 220 amino acids, 235 amino acids, 258 amino acids.

In some embodiments, the reference protein is a naturally-occurring protein. In some other embodiments, the reference protein is found in plants such as tropical plants. Non-limiting examples of a plant include at least one of capparis masaikai, oubli, serendipity berry, katemfe, miracle fruit berry, or lemba.

In some embodiments, the reference sweet protein is selected from the group consisting of Thaumatin, Monellin, Miraculin, Curculin, Brazzein and Mabinlin.

In some embodiments, the reference sweet protein is Thaumatin.

In some embodiments, the reference sweet protein is Monellin.

In some embodiments, the reference protein is Thaumatin-1 (GenBank Entry No. P02883; SEQ ID NO:1). In some embodiments, the reference protein is Thaumatin-2 (GenBank Entry No. P02884; SEQ ID NO:2).

In some embodiments, the reference protein is Monellin made out of chain A (GenBank Entry No. P02881; SEQ ID NO:3) and chain B (GenBank Entry No. P02882; SEQ ID NO:4).

In some embodiments, the reference protein is Miraculin (GenBank Entry No. P13087; SEQ ID NO:6).

In some embodiments, the reference protein is Curculin-1 GenBank Entry No. P19667; SEQ ID NO:7) or Curculin-2 (GenBank Entry No. Q6F495; SEQ ID NO:8).

In some embodiments, the reference protein is Brazzein (also known as: Defensin-like protein) (GenBank Entry No. P56552; SEQ ID NO:9).

In some embodiments, the reference protein is Mabinlin I/Sweet protein mabinlin-1 (GenBank Entry No. P80351; SEQ ID NO:10), Mabinlin II (also known as Sweet protein mabinlin-2) (GenBank Entry No. P30233; SEQ ID NO:11), Mabinlin III (also known as Sweet protein mabinlin-3) (GenBank Entry No. P80352; SEQ ID NO:12), Mabinlin IV (also known as Sweet protein mabinlin-4) (GenBank Entry No. P80353; SEQ ID NO:13) or mabinlin-1 chain A (GenBank Entry No. B9SA35; SEQ ID NO:14).

In some embodiments, the reference protein is sequence that is not found in nature and is thus called an artificial protein, or a synthetic protein or an engineered protein. The synthetic protein may comprise the entire or part of the amino acid sequence of the naturally occurring protein (all or part of the protein's polypeptide chains) or part thereof. For example, the reference protein may comprise a bond modification of a naturally occurring protein resulting in single polypeptide chain which corresponds to a naturally occurring protein, such that the at least two polypeptide chains of the wild type protein are covalently attached by other amino acids.

In some embodiments, the reference protein is a modified Monellin protein known as MNEI.

In some embodiments, the reference protein is a single chain Monellin (MNEI) protein (SEQ ID NO:5).

The novel modified proteins can be designed by various methods.

In some embodiments, design of the proteins is done by using computational tools or by expert protein design and structural biology methods e.g. site-directed mutagenesis, protein engineering or directed evolution as further described below. The inventors have developed computational methodologies which are based on sequence data of the reference flavor proteins, structural data of the reference flavor proteins and/or evolutionary data of the reference flavor proteins and other proteins that have local or global similarities to the reference flavor protein in sequence and/or in structural features. The ability of the computational methods developed and applied herein enabled the inventors to design proteins with specific amino acid substitutions that are energetically favorable and thus are predicted to have improved thermostability, halostability, pH-stability, shelf-life, folding and solubility features. Specifically, Computational Protein Design (CPD) was applied to focus on specific sites within the reference protein structure and/or sequence that are not necessarily functional binding sites to the receptor. In addition, the use of CPD allowed the inventors to limit the substitutions to a predefined set of amino-acids which fits the required improved features. The predefined set of amino-acids is both in the input data, i.e. the regions of the protein subjected to CPD, and in the output data, i.e. the location and types of amino acids allowed to be present in the resulting modified protein.

For example, using CPD it is possible to replace "non-ideal" amino acids (such as hydrophilic amino acids within a hydrophobic core or hydrophobic amino acids in the external surface region) to "ideal" amino acids (such as hydrophilic amino acids in the external surface region and hydrophobic amino acids within a hydrophobic core).

Without being bound by theory, it was suggested by the inventors that substituting hydrophobic amino acids in the external surface region into hydrophilic amino acids in the external surface region will reduce non-specific binding to the oral cavity and reduce the lingering after taste feeling.

The methodologies developed herein comprise searching for "stabilizing substitutions", e.g. amino acid substitutions that will decrease the overall energy of the protein structure. The overall energy may be calculated by application of known algorithms in the art. Non-liming examples of such algorithms include Rosetta, OSPREY (M. Hallen, J. Martin, et al., Journal of Computational Chemistry 2018; 39(30): 2494-2507 or EnCoM (Frappier V, Chartier M, Najmanovich R J. Nucleic Acids Res. 2015; 43(W1):W395-400). These CPD methods undergo focusing and filtering by an array of orthogonal methods such as evolutionary sequence and structural consensus, regular and high-temperature molecular dynamics (MD), correlated mutational analysis (CMA), visual inspection, as well as analysis of cavities, hydrophobic patches, unsatisfied hydrogen bonds and alike.

The amino acid substitutions are based on the following considerations: (a) surface electrostatic potential and (lack of) hydrophobic patches on the surface, (b) keeping the isoelectric point (pI) of the protein in a specific range, (c) analysis of the intra-protein cavities (d) dynamic stability including correlated mutational analysis, normal mode analysis and root mean square fluctuations (RMSF) in high-temperature dynamics), (e) entropic and/or enthalpic components of the energetics of the substitution, (f) visualization of the specific substitution. (g) types of amino-acids permitted in the family of related proteins; as reflected by an evolutionary conservation analysis of a curated multiple sequence alignment (MSA), (h) frequency of the substitution as reflected in low-pseudo-energy CPD calculations.

The computational methodologies include one or more of the following steps:

(1) multiple sequence alignment (MSA). In this step, sequences and/or protein with similarity to the target reference protein are searched in public databases. Based on this search, a multiple-sequence alignment (MSA) is constructed, the conservation rate is calculated. Based on which, a decision in regard to the level of CPD to be done is made. In non-conserved positions all amino acid (with or without Cysteine) are allowed during CPD, whereas for more conserved positions the CPD is limited to residues with similar properties to those found (e.g. charge, size and etc). This step involves limiting the substitutions in each substituted position, based on physical knowledge and conservation data.

(2) protein function analysis. In this step, a database of substitutions with known impact (on activity, structure, binding etc.) is constructed using prior knowledge. Substitutions, as well as adjacent positions (e.g. a distance of 0.5-1 nm from these positions), which are known based on prior knowledge to disturb the stability and/or function are limited during CPD and are not substituted.

(3) CPD. This step is done by designated software such as ROSETTA, OSPREY, SCWRL and alike. Before deterministic CPD is conducted, the reference protein 3D structure/model is energy minimized. For each reference protein, multiple models are considered.

(4) Selection: The models of proteins with lowest energy are collected. An MSA is computed on those models and a conserved sequence is determined. Based on biochemical and biophysical pre-knowledge, subsets of substitutions are chosen. Those subsets represent replacement at one or more positions that appear during CPD in high frequency. Each subset is then modelled on a 3D structure of the protein and energy minimized. The lowest energy subset is then selected for further computational and experimental validation.

One of the considerations used in CPD is the receptor binding site and the decision of whether or not to substitute amino acids in the binding region and its proximity. Determining amino acids residues in the protein that are important in the binding to the taste receptor may be generally done by single point substitution of various amino acids. As detailed herein the Examples, the inventors have used computational analysis for the characterization of putative binding sites in the taste receptor. The inventors have identified several novel binding sites in the taste receptor that bind to the reference proteins and the modified proteins.

The modified protein is based on the reference protein (amino acid sequence) and as such it should be noted that any feature/property/characterization described herein with respect to the modified protein is provided relative to the reference corresponding protein.

As described herein, the modified protein comprises an amino acid sequence having at least one, at least two, at least three, at least four, at least five, at least six, at least ten, at least fifteen, at least eighteen amino acid substitutions relative to a reference protein (reference amino acid sequence).

In some embodiments, the modified protein comprises at least two, at least three, at least four, at least five, at least six, at least ten, at least fifteen, at least eighteen amino acid substitutions relative to a reference protein (reference amino acid sequence).

In some embodiments, the modified protein comprises at least three, at least four, at least five, at least six, at least ten, at least fifteen, at least eighteen amino acid substitutions relative to a reference protein (reference amino acid sequence).

In some embodiments, the modified protein comprises between one to twenty amino acid substitutions relative to a reference protein (reference amino acid sequence), at times between two to ten amino acid substitutions, at times between three to ten amino acid substitutions, at times between three to six amino acid substitutions.

In some embodiments, the modified protein comprises at least one, at least two, at least three, at least four, at least five, at least six, at least ten, at least fifteen, at least eighteen amino acid substitutions relative to a reference protein (reference amino acid sequence), selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 and SEQ ID NO:14.

In some embodiments, the modified protein comprises at least one, at least two, at least three, at least four, at least five, at least six, at least ten, at least fifteen, at least eighteen amino acid substitutions relative to a reference protein denoted by SEQ ID NO:5.

In some embodiments, the modified protein comprises at least three, at least four, at least five, at least six, at least ten, at least fifteen, at least eighteen amino acid substitutions relative to a reference protein denoted by SEQ ID NO:5.

In some embodiments, the modified protein comprises at least one, at least two, at least three, at least four, at least five, at least six, at least ten, at least fifteen, at least eighteen amino acid substitutions relative to a reference protein denoted by SEQ ID NO:1.

In some embodiments, the modified protein comprises at least three, at least four, at least five, at least six, at least ten, at least fifteen, at least eighteen amino acid substitutions relative to a reference protein denoted by SEQ ID NO:1.

In some embodiments, the modified protein comprising an amino acid sequence that is between 40% to 99% identical to an amino acid sequence of the reference protein. In some embodiments, the modified protein comprising an amino acid sequence that is between 90% to 99% identical to the reference amino acid sequence.

In some embodiments, the modified protein comprising an amino acid sequence that is between 60% to 90% identical to the reference amino acid sequence. In some embodiments, the modified protein comprising an amino acid sequence that is between 70% to 90% identical to the reference amino acid sequence.

In some embodiments, the modified protein comprises an amino acid sequence having at least 60%, at least 65%, at least 70%, at least 75%, at least 80%, at least 85%, at least 90%, at least 95%, at least 99% identity with amino acid sequences selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 and SEQ ID NO:14.

In some embodiments, the modified protein comprises an amino acid sequence having at least 60%, at least 65%, at least 70%, at least 75%, at least 80%, at least 85%, at least 90%, at least 95%, at least 99% identity with amino acid sequences denoted by SEQ ID NO:5.

In some embodiments, the modified protein comprises an amino acid sequence having at least 60%, at least 65%, at least 70%, at least 75%, at least 80%, at least 85%, at least 90%, at least 95%, at least 99% identity with amino acid sequences denoted by SEQ ID NO:1.

In some embodiments, the modified protein comprises an amino acid sequence having between 60% to 99% identity with amino acid sequences selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 and SEQ ID NO:14.

In some embodiments, the modified protein comprises an amino acid sequence having between 90% to 99% identity with amino acid sequences selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 and SEQ ID NO:14.

In some embodiments, the modified protein comprises an amino acid sequence having between 90% to 99% identity with amino acid sequences denoted by SEQ ID NO:5.

In some embodiments, the modified protein comprises an amino acid sequence having between 80% to 99% identity with amino acid sequences denoted by SEQ ID NO:1.

The % identity between two or more amino acid sequences is determined for the two or more sequences when compared and aligned for maximum correspondence. In the context of the present disclosure, sequences (amino acid) as described herein having % identity are considered to have the same function/activity of the reference sequence to which identity is calculated to.

In some embodiments, the modified protein comprising an amino acid sequence that is between 40% to 99% similarity to an amino acid sequence of the reference protein. In some embodiments, the modified protein comprising an amino acid sequence that is between 90% to 99% similar to the reference amino acid sequence.

In some embodiments, the modified protein comprising an amino acid sequence that is between 60% to 90% similar to the reference amino acid sequence. In some embodiments, the modified protein comprising an amino acid sequence that is between 70% to 90% similar to the reference amino acid sequence.

In some embodiments, the modified protein comprises an amino acid sequence having at least 60%, at least 65%, at least 70%, at least 75%, at least 80%, at least 85%, at least 90%, at least 95%, at least 99% similarity with amino acid sequences selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 and SEQ ID NO:14.

In some embodiments, the modified protein comprises an amino acid sequence having at least 60%, at least 65%, at least 70%, at least 75%, at least 80%, at least 85%, at least 90%, at least 95%, at least 99% similarity with amino acid sequences denoted by SEQ ID NO:5.

In some embodiments, the modified protein comprises an amino acid sequence having at least 60%, at least 65%, at least 70%, at least 75%, at least 80%, at least 85%, at least 90%, at least 95%, at least 99% similarity with amino acid sequences denoted by SEQ ID NO:1.

In some embodiments, the modified protein comprises an amino acid sequence having between 60% to 99% similarity with amino acid sequences selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 and SEQ ID NO:14.

In some embodiments, the modified protein comprises an amino acid sequence having between 90% to 99% similarity with amino acid sequences selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 and SEQ ID NO:14.

In some embodiments, the modified protein comprises an amino acid sequence having between 90% to 99% similarity with amino acid sequences denoted by SEQ ID NO:5.

In some embodiments, the modified protein comprises an amino acid sequence having between 80% to 99% similarity with amino acid sequences denoted by SEQ ID NO:1.

In Sequence similarity or sequence homology as used herein refers to the amount (%) of amino acids that conserved with similar physicochemical properties, e.g. leucine and isoleucine.

In determining the sequence identity, the gaps are not counted and the sequence identity is relative to the shorter sequence of the two. In this connection, it should be noted that the length of the reference protein (amino acid sequence) may be the same as the modified protein (amino acid sequence) or may be different than the modified protein (amino acid sequence).

The term "amino acid sequence" and/or "polypeptide chain" are used to described a protein having an amino acid sequence or poly peptide chain. As such, the term "reference protein" is equivalent to the term "reference amino acid sequence" and the term "modified protein" is equivalent to the term "modified amino acid sequence". It should be noted that the terms "amino acid sequence" and/or "polypeptide chain" encompass sequences having a 3D structure as well as sequences with no 3D structure.

As part of the computational optimization process, the modified proteins may be selected from a large output population of amino acid sequences following computational- bioinformatic- or structural-biology analysis, based on energetic considerations, i.e. those sequences with low energy.

Energetic calculations can be applied on the entire amino acid sequence or alternatively be restricted to different regions or selected amino acids within the entire amino acid. In the latter (different regions or selected amino acids), the information may be integrated to obtain a measure for the entire protein.

Calculation of each one of the amino acid sequence (e.g a modified protein) may be done by combining physico-based and statistics-based potentials, such as by using the Rosetta Energy Unit (REU). Rosetta Energy Unit (REU) is an algorithm of the Rosetta software which is a package of algorithms for computational modeling and analysis of protein structures. The Rosetta software enables notable scientific advances in computational biology, including de novo protein design, enzyme design, ligand docking, and structure prediction of biological macromolecules and macromolecular complexes. Rosetta energy function is a combination of physical and statistical based potentials which does not match with any actual physical energy units. Rosetta energies are on an arbitrary scale and sometimes referred to as REU (for "Rosetta Energy Unit").

In some embodiments, the REU may be calculated for the entire protein sequence comprising the at least one amino acid substitution. In some other embodiments, the REU may be calculated for at least one region comprising the at least one amino acid substitution of the entire protein sequence. In some other embodiments, the REU may be calculated for at least one amino acid substitution in the entire protein sequence.

In some embodiments, the modified protein has an energy lower than −190 given in REU. In some embodiments, the modified protein has an energy of about −190 given in REU. In some embodiments, the modified protein has an energy of about −195 given in REU. In some embodiments, the modified protein has an energy lower than −195 given in REU. In some embodiments, the modified protein has an energy lower than −196 given in REU. In some embodiments, the modified protein has an energy lower than −197 given in REU. In some embodiments, the modified protein has an energy lower than −198 given in REU. In some embodiments, the modified protein has an energy of about −198 given in REU. In some embodiments, the modified protein has an energy lower than −198.4 given in REU. In some embodiments, the modified protein has an energy lower than −200 given in REU. In some embodiments, the modified protein has an energy lower than −206.4 given in REU. In some embodiments, the modified protein has an energy lower than −210 given in REU. In some embodiments, the modified protein has an energy lower than −214.6 given in REU.

In some embodiments, the modified protein has an energy lower than −270.11 given in REU. In some embodiments, the modified protein has an energy lower than −300 given in REU. In some embodiments, the modified protein has an energy lower than −350 given in REU. In some embodiments, the modified protein has an energy lower than −400 given in REU. In some embodiments, the modified protein has an energy lower than −410 given in REU. In some embodiments, the modified protein has an energy lower than −418 given in REU. In some embodiments, the modified protein has an energy lower than −420 given in REU. In some embodiments, the modified protein has an energy lower than −430 given in REU. In some embodiments, the modified protein has an energy lower than −433 given in REU.

In some embodiments, the modified protein has an energy of between −190 given in REU to about −214.6 given in REU. In some other embodiments, the modified protein has an energy of between −195 given in REU to about −214.6 given in REU. In some other embodiments, the modified protein has an energy of between −197 given in REU to about −214.6 given in REU.

As described herein, the modified protein may be a result of amino acid substitutions at various regions of the protein. "Regions of the protein" as used herein refers to an amino acid sequence or structural motif, that is part of the protein sequence (amino acid sequence) or protein structure. Non-limiting examples of protein regions include, protein surface, protein core, protein loop region, secondary structure capping region, disulfide region, binding-site region, linker region, hydrophobic-patch region, or protein hydrophobic region.

The amino acid substitution in the reference protein is not limited to a specific protein region or sequence. Regions of the reference protein that may include the amino acid substitutions may include the reference protein surface, the reference protein hydrophobic core, or reference protein regions called loop regions, edges of secondary structures (also denoted secondary structure capping regions), disulfide regions, binding-site regions, linker regions, hydrophobic-patch regions.

In some embodiments, the reference protein may be substituted within a confined region within the reference protein structure and/or sequence. In some embodiments, the reference protein may be substituted at the surface region. In some embodiments, the reference protein may be substituted at the core region. In some embodiments, the reference protein may be substituted of disulfide bonds. In some embodiments, the reference protein may be substituted at loop regions. In some embodiments, the two or more amino acids replacements are located on the surface of the reference protein.

In some embodiments, the reference protein may be substituted with a confined region that is not in the area adjacent to the predicted or known binding site of the reference protein to the receptor. In this context 'adjacent' may mean 4-7 Å from the binding interface.

In some embodiments, the reference protein may be substituted at different regions within the reference protein structure and/or sequence. In some embodiments, the reference protein may be substituted at least in the surface region, at the core region, at region of disulfide bonds or at loop regions and any combination thereof.

The protein surface region as used herein is the area with partial or full accessibility to solvent (SASA—solvent accessible surface area). The protein core region as used herein is the area not being accessible to solvent with an amino-acid relative SASA (solvent accessible surface area) of less than 50% or, for inner core, less than 20%.

In some embodiments, the modified protein comprises an amino acid sequence that has between 10% to 99%, at times between 20% to 99%, at times between 30% to 99%, at times between 40% to 99%, at times between 50% to 90%, at times 40%, 50%, 60%, 70%, 80%, 90%, 95%, 99% identity in the surface region relative to a reference amino acid sequence surface region.

In some embodiments, the modified protein comprises an amino acid sequence that has between 10% to 99%, at times between 20% to 99%, at times between 30% to 99%, at times between 40% to 99%, at times between 50% to 90%, at times 40%, 50%, 60%, 70%, 80%, 90%, 95%, 99% similarity in the surface region relative to an reference amino acid sequence surface region.

In some embodiments, the modified protein comprises an amino acid sequence that has between 10% to 99%, at times between 20% to 99%, at times between 30% to 99%, at times between 40% to 99%, at times between 50% to 90%, at times 40%, 50%, 60%, 70%, 80%, 90%, 95%, 99% identity in the hydrophobic core (hydrophobic-patch) region relative to an reference amino acid sequence hydrophobic core (hydrophobic-patch) region.

In some embodiments, the modified protein comprises an amino acid sequence that has between 10% to 99%, at times between 20% to 99%, at times between 30% to 99%, at times between 40% to 99%, at times between 50% to 90%, at times 40%, 50%, 60%, 70%, 80%, 90%, 95%, 99% similarity in the hydrophobic core (hydrophobic-patch) region relative to an reference amino acid sequence hydrophobic core (hydrophobic-patch) region.

In some embodiments, the modified protein comprises an amino acid sequence having between three (3) to forty (40) amino acid substitutions, between 4 to 30, between 5 to 30 amino acid substitutions in the surface region relative to a reference amino acid sequence surface region.

In some embodiments, the modified protein comprises an amino acid sequence having at least one (1), two (2), three (3), at least 4, at least 5, at least 6, at least 10, at least 15, at least 18, at least 20, at least 25 or 30 amino acid substitutions in the surface region relative to a reference amino acid sequence surface region.

In some embodiments, the modified protein comprises an amino acid sequence that is 20%, 30%, 50%, 80%, 90%, 95%, 98% identity in the core region relative to a reference amino acid sequence core region.

In some embodiments, the modified protein comprises an amino acid sequence that is 20%, 30%, 50%, 80%, 90%, 95%, 98% similarity in the core region relative to a reference amino acid sequence core region.

In some embodiments, the modified protein comprises an amino acid sequence having between one to five amino acid substitutions in the core region relative to a reference amino acid sequence core region.

In some embodiments, the modified protein comprises an amino acid sequence that has 90%, 95%, 99% identity in the region that binds to the receptor (receptor binding site) relative to the region that binds to the receptor in the reference amino acid sequence.

In some embodiments, the modified protein comprises an amino acid sequence that has 90%, 95%, 99% similarity in receptor binding site relative to the receptor binding sit in the reference amino acid sequence.

In some embodiments, the receptor binding site of the reference protein is not substituted in the modified protein.

In some embodiments, at least one of the disulfide bonds are removed and the regions around them redesigned with 8 to 20 substitutions around each of the disulfide bonds that are removed.

The Amino acids may be referred to herein by either their commonly known three letter symbols or by the one-letter symbols recommended by the IUPAC-IUB Biochemical Nomenclature Commission. Amino acid substitution (replacement) as used herein refers to a change from one amino acid to a different amino acid. This typically being due to point mutation in DNA sequence caused by nonsynonymous missense mutation which alters the codon sequence to code other amino acid instead of the references. An amino acid replacement may have an effect on function or structure of protein and this generally depends on how similar or dissimilar the replaced amino acids are, as well as on their position in the sequence or the structure. For example, the amino acid substitutions may be made on the basis of similarity in polarity, charge, solubility, hydrophobicity, hydrophilicity, bulkiness (or flexibility), beta-branching, aromaticity, ability to confer specific bonding interactions (hydrogen bonds, salt bridges, polar and non-polar interactions), pK, ability to bind sugars and other post-translational modifications and/or the amphipathic nature of the residues involved.

In some embodiments, the amino acid substitutions may be conservative replacement. Such a replacement encompasses a change in an amino acid into another amino acid exhibiting similar properties. Conservative amino acid replacements (also denoted as conservative amino acid "substitutions" or conservative amino acid mutations) is an amino acid replacement in a protein that changes a given amino acid to a different amino acid with similar biochemical, structural and/or chemical properties.

For example, amino acids may be sorted into six main classes on the basis of their structure and the general chemical characteristics of their side chains (R groups).

Aliphatic: Isoleucine (I), Leucine (L), Glycine (G), Alanine (A), Valine (V);

Hydroxyl or sulfur/selenium-containing: Serine (S), Cysteine (C), Threonine (T), Methionine (M);

Cyclic: Proline (P)

Aromatic: Phenylalanine (F), Tyrosine (Y), Tryptophan (W)

Basic: Histidine (H), Lysine (K), Arginine (R)

Acidic and their amides: Aspartate (D), Glutamate (E), Asparagine (N), Glutamine (Q).

In addition, each of the following groups contains other exemplary amino acids that are conservative substitutions for one another:

1) Very small: Alanine (A), Glycine (G);
2) Negative charge: Aspartic acid (D), Glutamic acid (E);
3) Polar (amidated carboxyl side chain): Asparagine (N), Glutamine (Q);
4) Positively charged: Arginine (R), Lysine (K);
6) Aromatic: Phenylalanine (F), Tyrosine (Y), Tryptophan (W), and occasionally also Histidine (H);
7) Small polar: Serine (S), Threonine (T);
8) Sulfur-containing: Cysteine (C), Methionine (M)
9) Small: Ala (A), Glycine (G), Serine (S).
10) Beta-branched: Valine (V), Isoleucine (I) and occasionally also Threonine (T);
11) Polar: Asparagine (N), Glutamine (Q), Serine (S), Threonine (T);

Nevertheless, there are numerous clustering of amino-acids yielding numerous amino acids indexes with each highlighting a different aspect of the amino acid characteristics—e.g. see hundreds of such indexes in the an index database https:www.genome.jp/aaindex/ Consequently, some of the conservative replacements may actually represent other features which are important for the fitness of the protein to industrial use in the food and beverage industry, e.g. non-specific binding to the tongue or other sensory profile aspects.

In addition, an additional conservation analysis is based on the following, nonpolar "hydrophobic" amino acids are selected from the group consisting of Valine (V), Isoleucine (I), Leucine (L), Methionine (M), Phenylalanine (F), Tryptophan (W), Cysteine (C), Alanine (A), Tyrosine (Y), Histidine (H), Threonine (T), Serine (S), Proline (P), Glycine (G), Arginine (R) and Lysine (K);

"polar" amino acids are selected from the group consisting of Arginine (R),

Lysine (K), Aspartic acid (D), Glutamic acid (E), Asparagine (N), Glutamine (Q);

"positively charged" amino acids are selected form the group consisting of Arginine (R), Lysine (K) and Histidine (H) and "acidic" amino acids are selected from the group consisting of Aspartic acid (D), Asparagine (N), Glutamic acid (E) and Glutamine (Q).

In some embodiments, the replacement is a radical replacement. A radical replacement (substitution) is an exchange of an amino acid into another amino acid with different properties.

The degree of sequence similarity and/or sequence identity between the reference protein and the modified protein may generally affect the properties of the modified proteins. For example, a large number of substitutions may affect the binding kinetics, folding kinetics, solubility, thermostability, halostability, pH stability, shelf-life, binding to non-aqueous particles (e.g. protein or fat in food matrix or hydrophobic regions in the oral cavity), 3D structure as well as its activity and related properties. The computational methods developed and applied herein, provide a thorough understanding on putative amino acids residues for substitution that will result in improved modified proteins.

In accordance with some aspects, the reference protein is MNEI having an amino acid sequence denoted by SEQ ID NO:5. As shown in Example 1 below, CPD analysis have revealed several amino acids substitutions that were suggested to be important for substitutions.

Thus, in accordance with some aspects, the present disclosure relates to a modified protein comprising an amino acid sequence denoted by SEQ ID NO:5, comprising at least one amino acid, wherein the modified protein has at least one improved food-related property compared with SEQ ID NO:5.

In some embodiments, the reference protein is MNEI having an amino acid sequence denoted by SEQ ID NO:5 and the amino acid to be substituted is E2. In some embodiments, the reference protein is MNEI having an amino acid sequence denoted by SEQ ID NO:5 and the amino acid to be substituted is 18. In some embodiments, the reference protein is MNEI having an amino acid sequence denoted by SEQ ID NO:5 and the amino acid to be substituted is F11. In some embodiments, the reference protein is MNEI having an amino acid sequence denoted by SEQ ID NO:5 and the amino acid to be substituted is N14. In some embodiments, the reference protein is MNEI having an amino acid sequence denoted by SEQ ID NO:5 and the amino acid to be substituted is G16. In some embodiments, the reference protein is MNEI having an amino acid sequence denoted by SEQ ID NO:5 and the amino acid to be substituted is K17. In some embodiments, the reference protein is MNEI having an amino acid sequence denoted by SEQ ID NO:5 and the amino acid to be substituted is F18. In some embodiments, the reference protein is MNEI having an amino acid sequence denoted by SEQ ID NO:5 and the amino acid to be substituted is V20. In some embodiments, the reference protein is MNEI having an amino acid sequence denoted by SEQ ID NO:5 and the amino acid to be substituted is D21. In some embodiments, the reference protein is MNEI having an amino acid sequence denoted by SEQ ID NO:5 and the amino acid to be substituted is E23. In some embodiments, the reference protein is MNEI having an amino acid sequence denoted by SEQ ID NO:5 and the amino acid to be substituted is Q28. In some embodiments, the reference protein is MNEI having an amino acid sequence denoted by SEQ ID NO:5 and the amino acid to be substituted is R31. In some embodiments, the reference protein is MNEI having an amino acid sequence denoted by SEQ ID NO:5 and the amino acid to be substituted is T33. In some embodiments, the reference protein is MNEI having an amino acid sequence denoted by SEQ ID NO:5 and the amino acid to be substituted is N35. In some embodiments, the reference protein is MNEI having an amino acid sequence denoted by SEQ ID NO:5 and the amino acid to be substituted is C41. In some embodiments, the reference protein is MNEI having an amino acid sequence denoted by SEQ ID NO:5 and the amino acid to be substituted is L62. In some embodiments, the reference protein is MNEI having an amino acid sequence denoted by SEQ ID NO:5 and the amino acid to be substituted is V64. In some embodiments, the reference protein is MNEI having an amino acid sequence denoted by SEQ ID NO:5 and the amino acid to be substituted is Y65. In some embodiments, the reference protein is MNEI having an amino acid sequence denoted by SEQ ID NO:5 and the amino acid to be substituted is S67. In some embodiments, the reference protein is MNEI having an amino acid sequence denoted by SEQ ID NO:5 and the amino acid to be substituted is A73. In some embodiments, the reference protein is MNEI having an amino acid sequence denoted by SEQ ID NO:5 and the amino acid to be substituted is R84. In some embodiments, the reference protein is MNEI having an amino acid sequence denoted by SEQ ID NO:5 and the amino acid to be substituted is F89. In some embodiments, the reference protein is MNEI having an amino acid sequence denoted by SEQ ID NO:5 and the amino acid to be substituted is at least one of the following amino acids E2, I8, F11, N14, G16, K17, F18, V20, D21, E23, Q28, R31, T33, N35, C41, L62, V64, S67, A73, R84 or F89.

In some embodiments, the at least one amino acid substitution is a conservative substitution. In some embodiments, the at least one amino acid substitution is a radical substitution. In some embodiments, two or more amino acids are substituted.

In some embodiments, the reference protein is MNEI having an amino acid sequence denoted by SEQ ID NO:5 comprising at least one substitution of E2 into a polar uncharged amino acid. In some embodiments, the reference protein is MNEI having an amino acid sequence denoted by SEQ ID NO:5 comprising at least one substitution E2S, E3T, E2N or E2Q.

In some embodiments, the reference protein is MNEI having an amino acid sequence denoted by SEQ ID NO:5 comprising at least one substitution of I8 into a polar uncharged amino acid or a hydrophobic amino acid. In some embodiments, the reference protein is MNEI having an amino acid sequence denoted by SEQ ID NO:5 comprising at least one substitution I8T or I8V.

In some embodiments, the reference protein is MNEI having an amino acid sequence denoted by SEQ ID NO:5 comprising at least one substitution of F11 into a charged amino acid. In some embodiments, the reference protein is MNEI having an amino acid sequence denoted by SEQ ID NO:5 comprising at least one substitution F11D or F11E.

In some embodiments, the reference protein is MNEI having an amino acid sequence denoted by SEQ ID NO:5 comprising at least one substitution of N14 into a charged amino acid. In some embodiments, the reference protein is MNEI having an amino acid sequence denoted by SEQ ID NO:5 comprising at least one substitution N14K or N14E.

In some embodiments, the reference protein is MNEI having an amino acid sequence denoted by SEQ ID NO:5 comprising at least one substitution of G16 into a hydrophobic amino acid. In some embodiments, the reference protein is MNEI having an amino acid sequence denoted by SEQ ID NO:5 comprising at least one substitution G16A.

In some embodiments, the reference protein is MNEI having an amino acid sequence denoted by SEQ ID NO:5 comprising at least one substitution of K17 into charged amino acid. In some embodiments, the reference protein is MNEI having an amino acid sequence denoted by SEQ ID NO:5 comprising at least one substitution K17E or K17R.

In some embodiments, the reference protein is MNEI having an amino acid sequence denoted by SEQ ID NO:5 comprising at least one substitution of F18 into charged amino acid or hydrophobic amino acid. In some embodiments, the reference protein is MNEI having an amino acid sequence denoted by SEQ ID NO:5 comprising at least one substitution F18D.

In some embodiments, the reference protein is MNEI having an amino acid sequence denoted by SEQ ID NO:5 comprising at least one substitution of V20 into an hydrophobic amino acid. In some embodiments, the reference protein is MNEI having an amino acid sequence denoted by SEQ ID NO:5 comprising at least one substitution V20A.

In some embodiments, the reference protein is MNEI having an amino acid sequence denoted by SEQ ID NO:5 comprising at least one substitution of D21 into a charged amino acid. In some embodiments, the reference protein is MNEI having an amino acid sequence denoted by SEQ ID NO:5 comprising at least one substitution D21K, D21R or D21E.

In some embodiments, the reference protein is MNEI having an amino acid sequence denoted by SEQ ID NO:5 comprising at least one substitution of E23 into a polar uncharged amino acid or a hydrophobic amino acid. In some embodiments, the reference protein is MNEI having an amino acid sequence denoted by SEQ ID NO:5 comprising at least one substitution E23T or E23A.

In some embodiments, the reference protein is MNEI having an amino acid sequence denoted by SEQ ID NO:5 comprising at least one substitution of Q28 into a charged amino acid. In some embodiments, the reference protein is MNEI having an amino acid sequence denoted by SEQ ID NO:5 comprising at least one substitution Q28K.

In some embodiments, the reference protein is MNEI having an amino acid sequence denoted by SEQ ID NO:5 comprising at least one substitution of R31 into a hydrophobic amino acid. In some embodiments, the reference protein is MNEI having an amino acid sequence denoted by SEQ ID NO:5 comprising at least one substitution R31V.

In some embodiments, the reference protein is MNEI having an amino acid sequence denoted by SEQ ID NO:5 comprising at least one substitution of T33 into a hydrophobic amino acid. In some embodiments, the reference protein is MNEI having an amino acid sequence denoted by SEQ ID NO:5 comprising at least one substitution T33V.

In some embodiments, the reference protein is MNEI having an amino acid sequence denoted by SEQ ID NO:5 comprising at least one substitution of N35 into a hydrophobic amino acid. In some embodiments, the reference protein is MNEI having an amino acid sequence denoted by SEQ ID NO:5 comprising at least one substitution N35V.

In some embodiments, the reference protein is MNEI having an amino acid sequence denoted by SEQ ID NO:5 comprising at least one substitution of C41 into a charged amino acid or a polar uncharged amino acid. In some embodiments, the reference protein is MNEI having an amino acid sequence denoted by SEQ ID NO:5 comprising at least one substitution C41R or C41S.

In some embodiments, the reference protein is MNEI having an amino acid sequence denoted by SEQ ID NO:5 comprising at least one substitution of L62 into a charged amino acid or a polar uncharged amino acid. In some embodiments, the reference protein is MNEI having an amino acid sequence denoted by SEQ ID NO:5 comprising at least one substitution L62I.

In some embodiments, the reference protein is MNEI having an amino acid sequence denoted by SEQ ID NO:5 comprising at least one substitution of V64 L62 into a charged amino acid or a polar uncharged amino acid. In some embodiments, the reference protein is MNEI having an amino acid sequence denoted by SEQ ID NO:5 comprising at least one substitution V64F.

In some embodiments, the reference protein is MNEI having an amino acid sequence denoted by SEQ ID NO:5 comprising at least one substitution of Y65.

In some embodiments, the reference protein is MNEI having an amino acid sequence denoted by SEQ ID NO:5 comprising at least one substitution of S67 into a polar uncharged amino acid. In some embodiments, the reference protein is MNEI having an amino acid sequence denoted by SEQ ID NO:5 comprising at least one substitution S67N.

In some embodiments, the reference protein is MNEI having an amino acid sequence denoted by SEQ ID NO:5 comprising at least one substitution of A73 into a hydrophobic amino acid. In some embodiments, the reference protein is MNEI having an amino acid sequence denoted by SEQ ID NO:5 comprising at least one substitution A73G.

In some embodiments, the reference protein is MNEI having an amino acid sequence denoted by SEQ ID NO:5 comprising at least one substitution of R84 into a hydrophobic amino acid. In some embodiments, the reference protein is MNEI having an amino acid sequence denoted by SEQ ID NO:5 comprising at least one substitution R84L.

In some embodiments, the reference protein is MNEI having an amino acid sequence denoted by SEQ ID NO:5 comprising at least one substitution of F89 into a polar uncharged amino acid. In some embodiments, the reference protein is MNEI having an amino acid sequence denoted by SEQ ID NO:5 comprising at least one substitution F89S.

In some embodiments, the reference protein is MNEI having an amino acid sequence denoted by SEQ ID NO:5 and the amino acid to be substituted is at least one of the following amino acids E2, I8, F11, N14, G16, K17, F18, V20, D21, E23, Q28, R31, T33, N35, C41, L62, V64, S67, A73, R84 or F89.

Amino acid substitutions in MNEI were previously reported including multiple mutations. For example, Zheng et al reported novel double mutant MNEI-based proteins with improved sweetness and stability. Specifically, Zheng et al demonstrated that a single substitution E2N in MNEI resulted in a 3-fold improved sweetness and a slight reduced stability. Zheng et al further showed that introducing an additional substitution, E23A or Y65R, in addition to the E2N substitution (e.g. E2N/E23A, E2N/Y65R), had no effect on the sweetness.

As described above, amino acid E23 was identified during CPD analysis to be important for protein stability. Thus, the charged glutamate in position 23 (E23) of MNEI that is relatively buried was replaced to a hydrophobic amino acid.

As also shown herein in the examples below, the modified protein comprising three substitutions in amino acids at positions E2, E23 and Y65, surprisingly resulted in a resulted in a 6 to 7-fold improved sweetness and potentially other improved properties such as sensory profile and synergy with other ingredients (including other sweeteners such as stevia). Without being bound by theory, it was suggested that the triple substitution results in a synergistic effect on the sweetness in the modified protein. As also shown below, the modified protein comprising three substitutions in amino acids at positions E2, E23 and Y65 has an REU in the same range as MNEI, suggesting that the REU indicate that the substitutions do not interfere with stability.

Thus, in accordance with some aspects, the present disclosure relates to a modified protein comprising an amino acid sequence denoted by SEQ ID NO:5, comprising at least three amino acid substitutions at residues E2, E23 and Y65 of SEQ ID NO:5, wherein the modified protein has at least one improved food-related property compared with SEQ ID NO:5.

It should be understood that according with such embodiments, the reference protein is MNEI denoted by SEQ ID NO:5 and the design protein include at least three substitutions at amino acids E2, E23 and Y65 of SEQ ID NO:5.

Each one of the amino acids E2, E23 and Y65 may be substituted by any amino acid. In some embodiments, the amino acid substitution at amino acid (residue) E2 may be any one of E2R, E2H, E2K, E2D, E2S, E2T, E2N, E2Q, E2C, E2G, E2P, E2A, E2V, E2I, E2L, E2M, E2F, E2Y, E2W. In some embodiments, the amino acid substitution at amino acid (residue) E23 may be any one of E23R, E23H, E23K, E23D, E23S, E23T, E23N, E23Q, E23C, E23G, E23P, E23A, E23V, E23I, E23L, E23M, E23F, E23Y, E23W. In some embodiments, the amino acid substitution at amino acid (residue) Y65 may be any one of Y65R, Y65H, Y65K, Y65D, Y65E, Y65S, Y65T, Y65N, Y65Q, Y65C, Y65G, Y65P, Y65A, Y65V, Y65I, Y65L, Y65M, Y65F and Y65W.

In some embodiments, at least one, at least two or at least three of the at least three amino acid substitutions in a reference protein being MNEI is a conservative substitution.

In some embodiments, at least one of the at least three amino acid to be substituted is amino acid E2 and is substituted to a charged residue, optionally to a negative charged amino acid. In some embodiments, the at least one of the at least three amino acid to be substituted is amino acid E2 and is substituted to an acidic residue. In some embodiments, the at least one of the at least three amino acid to be substituted is amino acid E2 and is substituted to a polar residue. In some embodiments, the at least one of the at least three amino acid to be substituted is E2N, E2D, E2Q, E2R or E2K. In some embodiments, the at least one of the at least three amino acid to be substituted is E2N, E2D or E2Q. In some embodiments, the at least one of the at least three amino acid to be substituted is E2N.

In some embodiments, at least one of the at least three amino acid to be substituted is amino acid E23 and is substituted to a charged residue, optionally to a negative charged amino acid. In some embodiments, the at least one of the at least three amino acid to be substituted is amino acid E23 and is substituted to an acidic residue. In some embodiments, the at least one of the at least three amino acid to be substituted is amino acid E23 and is substituted to a polar residue. In some embodiments, the at least one of the at least three amino acid to be substituted is E23N, E23D, E23Q, E23R or E23K. In some embodiments, the at least one of the at least three amino acid to be substituted is E23N, E23D or E23Q.

In some embodiments, at least one of the at least three amino acid to be substituted is amino acid Y65 and is substituted to an aromatic residue. In some embodiments, the at least one of the at least three amino acid to be substituted is amino acid Y65 and is substituted to a non-polar hydrophobic residue. In some embodiments, the at least one of the at least three amino acid to be substituted is Y65F, Y65W, Y65H, Y65V, Y65I, Y65L, Y65M, Y65C, Y65A, Y65T, Y65S, Y65P, Y65G, Y65K and Y65R. In some embodiments, the at least one of the at least three amino acid to be substituted is Y65K and Y65R.

In some embodiments, the reference protein is MNEI and the at least one of the at least three amino acid substitutions are selected from the group consisting of E2N, E2D, E2Q, E2R, E2K, E23N, E23D, E23Q, E23R, E23K, Y65F, Y65W, Y65H, Y65V, Y65I, Y65L, Y65M, Y65C, Y65A, Y65T, Y65S, Y65P, Y65G, Y65K and Y65R.

In some embodiments, the reference protein is MNEI and the at least three substitutions are selected from the group consisting of E2N, E23V, E23A, Y65K, and Y65R.

In some embodiments, the reference protein is MNEI and the at least three substitutions are E2N, E23V and Y65K.

In some embodiments, the reference protein is MNEI and the at least three substitutions are E2N, E23A and Y65R.

In some embodiments, the modified protein has an amino acid sequence of:
GNWEIIDIGPFTQNLGK-
FAVDEVNKIGQYGRLTFNKVIRPCMKKTIYENEG
FREIKGYEYQLYVKASDKLFRADISEDYKTR-
GRKLLRFNGPVPPP (SEQ ID NO: 16). SEQ ID NO:16 is denoted herein as DM08.

In some embodiments, the modified protein has an amino acid sequence of:
GNWEIIDIGPFTQNLGK-
FAVDEANKIGQYGRLTFNKVIRPCMKKTIYENEG
FREIKGYEYQLYVRASDKLFRADISEDYKTR-
GRKLLRFNGPVPPP (SEQ ID NO: 17). SEQ ID NO:17 is denoted herein as DM09.

In accordance with some aspects, the reference protein has an amino acid sequence denoted by SEQ ID NO:1. As shown in Example 2 below, CPD analysis have revealed several amino acids substitutions that were suggested to be important for substitutions.

Thus, in accordance with some aspects, the present disclosure relates to a modified protein comprising an amino acid sequence denoted by SEQ ID NO:1, comprising at least one amino acid, wherein the modified protein has at least one improved food-related property compared with SEQ ID NO:1.

In some embodiments, the reference protein has an amino acid sequence denoted by SEQ ID NO:1 and the amino acid to be substituted is at least one of the following amino acids A1, T2, F3, E4, V, R8, S10, Q30, N32, S33, E35, S36, W37, T38, I39, N40, A52, A88, N93, I100, N104, M112, N113, F114, 5115, T117, T118, R119, V124, R125, A127, A128, D129, V131, G132, Q133, A136, K137, K139, A140, G142, A148, F152, T154, Y157, G165, P166, E168, Y169, R171, L176, D179, V191, 5196, 5197, N198, R200, T202, T206 or A207.

As described herein, the modified protein described herein has an improved food-related property. The protein's sweetness profile such as sweetness potency (sugar-like flavor), lack of off-taste, reduced onset time and reduced lingering taste of the modified protein may be determined by any known taste test that is known in the art. For example, comparison to the sweetness of sucrose or other sweeteners can be made by a taste panel and the sweetness potency may be graded as detailed in the examples below.

The comparison may be by determine the threshold of the modified protein as compared to a known sweetener, such as sucrose, for example by determining the minimal concentration required to evoke the sensation of sweetness or the assessment of the sweetness profile including characteristics such as sweetness profile, sweetness onset time, lingering taste, mouthfeel, aftertaste, off-taste, and masking of unwanted tastes.

As used herein the term sweetening-affecting properties encompass a sweet sensation determined by at least one of a sweetness threshold of about 0.28 mg/L or higher, sweetness duration of about between 1 to 20 seconds, at times between 2 to 18 seconds, at times between 2-4 seconds The modified protein similar to the reference protein binds to the sweet receptor.

In some embodiments, the modified protein has perceived sweetness threshold that is 300-16,000 higher than sugar on a weight basis.

The sensory profile includes taste kinetics which is usually a gaussian showing taste intensity over time i.e. onset duration (time till feeling taste), taste duration and time of lingering taste (corresponding to the tail of the gaussian). Additional features include off-taste (e.g. due to binding to other receptors), roundness of the taste, metallic and other side-tastes, synergy with other ingredients (e.g. masking and enhancing other flavors or their unwanted tastes, such as stevia) and alike.

In some embodiments, the modified protein is characterized by at least one of the following being equal or improved relative to the reference protein: (1) structural thermal stability (2) functional thermal stability, (3) pH stability (4) a solubility in water or in a partly aqueous milieu (e.g. foods containing fat) or (5) shelf life stability.

In some embodiments the modified protein has structural thermal stability being equal or improved relative to the reference protein.

The term "structural thermal stability" or "thermal stability" as used herein refers to the ability of the modified protein to retain its 3D structure at temperatures above that of the reference protein. The 3D structural stability of a protein can be measured by any method known in the art, such as Circular Dichroism (CD), or thermal shift assays such as Differential Scanning Fluorimetry (DSF) or Differential Scanning calorimetry (DSC). The 3D structure of a protein may have an effect on the function of the protein. Notably, the shelf-life and thermal stability required for food and beverage products may be related to the structural thermal stability and consists of different measurables e.g. pasteurization can be applied by different protocols and is related to the heat resistance of retaining the protein structure over a very short time.

In some embodiments the modified protein has functional thermal stability being equal or higher relative to the reference protein. The term "functional thermal stability" as used herein refers to the ability of the modified protein to retain its function after exposure to high temperatures compared with the reference protein.

In some embodiments, the modified protein herein may maintain sweetness effect at higher temperature or after exposure to higher temperature for a time which may be limited. In other words, there is no sensed change in the sweetness- or sensory-profile after exposure of the product to a temperature above room temperature, at times, up to 50° C., at times up to 100° C., or even up to 150° C. The protein function, e.g. sweetest may be measured by sensational tests.

In some embodiments the modified protein has pH stability being equal or higher relative to the reference protein. The pH stability refers to a stability of the modified protein at a wider pH range relative to the reference protein, namely the modified protein maintains the 3D structure and/or function) after exposure of the product to any pH from 3 to 8, at times, at a pH of between 4 to 8. For example, a soda like cola has a pH of 2.3-2.5 where some of the sweet proteins are not stable and lose functionality immediately or after a time that is shorter than the regular shelf-life of the beverage.

In some embodiments the modified protein has a solubility being higher relative to the reference protein. Solubility may be in an aqueous, partly aqueous or non-aqueous milieu such as foods containing fat.

In some embodiments the modified protein has improved shelf life relative to the reference protein. Improved shelf life refers to no sensed change in the sweetness (function) or physical deterioration of a product comprising the composition (e.g. color change, phase separation etc.) after exposure of the product to any temperature up to 150° C., at times, to any temperature between 4° C. to 150°, or to 100°.

In some other embodiments, the modified protein is characterized by at least one of the following being equal or improved relative to the reference protein (1) folding kinetics, (2) post-translational modification (e.g. glycosylation) pattern of the protein is different relative to the reference protein, (3) the number of disulfide bonds are lower relative to the reference protein.

In some embodiments the modified protein has a folding kinetics equal or higher relative to the reference protein. Namely, the protein folding rate from an unfolded or partially-folded structure is faster (as assessed in silico e.g. by molecular dynamics or by experimental in vitro or in vivo methods). Alternatively, faster folding kinetics also refers to slower unfolding kinetics in denaturation experiments e.g. by denaturant titrations (e.g. guanidinium chloride and/or high-concentration urea) or other methods.

In some embodiments, the modified protein is characterized by expression yield equal or higher relative to the reference protein in the host organism assessed.

In some embodiments the modified protein has a PI value of between 7.8 to 8.4.

The modified protein described herein being characterized by a sweet taste as well as potentially other taste effects (masking unwanted tastes, less aftertaste, less lingering taste, less off-taste, less lingering taste onset, umami taste) may be used as a sweetener in the preparation of a product for oral delivery.

The modified protein can be used as a flavor modifying agent or a flavor enhancing agent.

The protein described herein is for use as an oral product. In some embodiments, the product is a food product, a food supplementary product or a medicament. For the preparation of a product, the proteins described herein may be combined with any food grade additive. The food product may be provided and in used in any solid dry form, including, without being limited thereto, fine powder, lyophilizate, granulate, tablets, etc. In some embodiments, the composition is provided in liquid form, for example, as a solute in water (aqueous solution).

The product comprising the proteins may have various applications. This include, without being limited thereto (each of the following constituting a separate embodiment of the present disclosure), utilization as a sweetener, flavor, enhancer or masker in the food and beverages industry (soft drinks, ready-to-drink beverages, syrups, functional drinks, sports drinks etc.), in the dairy industry, i.e., dairy products, yoghurts and puddings, in the pharmaceutical industry, in the naturopathic industry, nutraceutical industry and other healthcare products (e.g. toothpaste, mouthwash); candy and gum industry, or any other application that requires the use of a flavor modifying composition as an excipient or additive.

The product may comprises additional food ingredients. In some embodiments, the food ingredient is a sweetener, for example stevia. As shown in the Examples below, combination of the modified protein described herein and stevia produced a synergetic effect. Thus, in some embodiments, the product comprises at least one modified protein denoted by SEQ ID NO:16 or SEQ ID NO:17 and stevia.

It should be noted that the modified proteins according to the invention can be produced by any method known in the art, for example the protein can be produced synthetically, by recombinant DNA technology or by protein production in microorganisms via fermenters or in plants or in plant callus or other bioreactors. In some embodiments, the modified proteins may be produced in bacteria, such as *E. Coli*. In some other embodiments, the modified proteins may be produced yeast, such as *Saccharomyces cerevisiae* or *Pichia pastoris*. In some embodiments, the DNA sequence of the chosen amino acid sequence is optimized in the RNA and DNA levels. In the RNA level this includes minimization of RNA secondary structures to ensure quick insertion into the ribosome. In the DNA level this includes codon optimization to the host organism (taking into account the RNA-level optimization). The codon-usage optimization provides preference for using the most abundant tRNA in the host organism for each amino acid expressed.

With regards to the above, it is to be understood that, where provided, percentage values such as, for example, 10%, 50%, 120%, 500%, etc., are interchangeable with "fold change" values, i.e., 0.1, 0.5, 1.2, 5, etc., respectively.

All scientific and technical terms used herein have meanings commonly used in the art unless otherwise specified. The definitions provided herein are to facilitate understanding of certain terms used frequently herein and are not meant to limit the scope of the present disclosure.

As used herein the term "about" refers to ±10% The terms "comprises", "comprising", "includes", "including", "having" and their conjugates mean "including but not limited to". The term "consisting essentially of" means that the composition, method or structure may include additional ingredients, steps and/or parts, but only if the additional ingredients, steps and/or parts do not materially alter the basic and novel characteristics of the claimed composition, method or structure. The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range.

It must be noted that, as used in this specification and the appended claims, the singular forms "a", "an" and "the" include plural referents unless the content clearly dictates otherwise.

NON-LIMITING EXAMPLES

Example 1—Design and Characterization of MNEI Based Proteins

Example 1A: Design of MNEI Based Proteins

Design of MNEI-based proteins was done as follows: Single-chain monellin, MNEI, is a polypeptide composed of 96 amino acids, with molecular weight of ~11 kD and pI ~8.7. MNEI is denoted as SEQ ID NO:5.
Computational Methods As described above, the computational and human-expert analysis provides a reduced sequence space which can be further analyzed computationally or by an expert or experimentally or by a combination of these methods. Such analysis can be applied to individual amino acids, to clusters of amino-acids or to other combinations.

During the CPD process, amino acid replacements were allowed in specific regions which are less prone to be part of the binding site to the receptor e.g. around the helix and the non-exposed side of the beta-sheet which forms the core of the protein. ROSETTA run had results in 160K models. When the energy of all models was drawn, the outcome graph has the form of a logit function. Logit function (also known as log-odds) is the logarithm of the odds p/(1−p) where p is the probability. It is the inverse of the sigmoidal "logistic" function.

For further analysis the 5K lowest models were selected. Plotting the number of replacements (compared to MNEI) as function of REU gave a Gaussian distribution, showing that the populations are normal and valid for further analysis.

Table 1 shows that CPD performed on specific residues that span all the reference protein sequence suggested replacement in alpha-helix, beta-sheets and loops spanning all secondary structure elements of MNEI.

Importantly, non-trivial replacements were identified. For example, the replacement of V64F introduced a large nonbeta-sheet amino acid in a beta-sheet. Most replacements in beta-sheets regions are to beta-sheet amino-acids in order to protect its tertiary structure.

From Table 1 it can also be seen that for most buried positions, the CPD suggestion is for replacements to hydrophobic residues such as Leu, Ala or Val. Such replacements are likely to stabilize the protein's core and hence promote stability and shelf-life. Nevertheless, CPD does result in the few cases where the replacements are to polar or charged residues (e.g. N14K). Such replacements are unlikely to stabilize MNEI's core. Upon careful inspection it seems that such surprising replacements are likely to form hydrogen-bonds with other residues or with water molecules.

Surface fully- or partially-exposed position are mostly replaced to polar or charged residues that can interact with water and stabilize MNEI. However, there are unanticipated cases in which CPD suggest replacement to hydrophobic residue, for example R84L. Such cases are unexpected and unique and are not likely explained by inspection of the 3D structure of MNEI.

TABLE 1

Summary of amino acid substitutions in MNEI that were found during CPD analysis.

| Amino acid type and location in MNEI | Region of the amino acid in MNEI | Secondary structure region of the amino acid | CPD high-preference suggested substitution |
|---|---|---|---|
| I8 | Exposed | Loop | T/I/V |
| F11 | Exposed | Helix | F/D/E |
| N14 | Mostly buried | Helix | K/E |
| G16 | Buried | Helix | G/A |
| K17 | Exposed | Helix | K/E/R |
| F18 | Partially exposed | Helix | F/D |
| V20 | Mostly buried | Helix | V/A |
| D21 | Exposed | Helix | K/R/E |
| E23 | Mostly buried | Helix | T/A |
| Q28 | Exposed | Loop | K |
| R31 | Exposed | Loop | V |
| T33 | Buried | Loop | V |
| N35 | Exposed | Beta | V |
| C41 | Mostly buried | Loop | R/S |
| L62 | Buried | Beta | I/L |
| V64 | Buried | Beta | F |
| S67 | Partially exposed | Loop | N |
| A73 | Buried | Beta | G/A |
| R84 | Exposed | Beta | L |
| F89 | Mostly buried | Beta | S/F |

In addition, during CPD process, specific amino-acids were selected following analysis of the proteins, amino acid E23 was identified as an important residue for stability. The contribution of this amino acid alone or in combination was tested by CPD. Table 2 shows the REU values of such analysis.

TABLE 2

CPD analysis of selected amino acids in MNEI

| Amino acid substitution | REU |
|---|---|
| E2H | −197.945 |
| E2M | −198.603 |
| E2N | −201.348 |
| E2Q | −201.655 |
| E2N/E23A | −198.488 |
| E23A | −199.430 |
| E23Q | −198.000 |
| E23T | −197.985 |
| E23V | −198.724 |
| E23S | −197.037 |

Table 3 shows sequence of modified MNEI based proteins (designer proteins) that were designed as detailed above.

TABLE 3

Sequence of modified proteins

| SEQ ID NO: | Sequence |
|---|---|
| SEQ ID NO: 15 (DM03) | GNWEIIDTGPFTQKLGKFAVDEANKIGKYGTLTFTK VIRPTMKKTIYENEGFREIKGYEYQLYVKANDKLFR ADISEDYKTRGLKLLRFNGPVPPP |
| SEQ ID NO: 16 (DM8) | GNWEIIDIGPFTQNLGKFAVDEVNKIGQYGRLTFNK VIRPCMKKTIYENEGFREIKGYEYQLYVKASDKLFR ADISEDYKTRGRKLLRFNGPVPPP |
| SEQ ID NO: 17 (DM9) | GNWEIIDIGPFTQNLGKFAVDEANKIGQYGRLTFNK VIRPCMKKTIYENEGFREIKGYEYQLYVRASDKLFR ADISEDYKTRGRKLLRFNGPVPPP |
| SEQ ID NO: 18 (DM10) | GEWEIIDIGPFTQNLGKFAVDEENKIGKYGTLTFTK VIRPCMKKTIYENEGFREIKGYEYQLYVYANDKLFR ADISEDYKTRGRKLLRFNGPVPPP |
| SEQ ID NO: 19 (DM11) | GEWEIIDTGPFTQKLGKFAVDEENKIGQYGRLTFNK VIRPTMKKTIYENEGFREIKGYEYQLYVYASDKLFR ADISEDYKTRGLKLLRFNGPVPPP |
| SEQ ID NO: 20 (DM12) | GEWEIIDTGPFTQNLGKFAVDEENKIGQYGRLTFNK VIRPTMKKTIYENEGFREIKGYEYQLYVYASDKLFR ADISEDYKTRGLKLLRFNGPVPPP |

The proteins were expressed in 1 L high density fermentation and purified to >90% level by ion exchange chromatography followed by size exclusion chromatography.

Table 4 shows the structural characterization of the novel designer proteins.

TABLE 4 structural characterization of modified MNEI based proteins

| | MNEI | DM03 E2N/I8T/N14K/ E23A/Q28K/R31T/ N35T/C41T/Y65K/ S67N/R84L | DM08 E2N/E23V/ Y65K | DM09 E2N/E23A/ Y65R | DM10 Q28K/R31T/ N35T/S67N | DM11 I8T/N14K/ C41T/R84L | DM12 I8T/C41T |
|---|---|---|---|---|---|---|---|
| Number of amino acid substitutions relative to MNEI | 0 | 11 | 3 | 3 | 4 | 4 | 2 |
| energy as given in Rosetta Energy Unit (REU) | −198.410 | −205.134 | −198.212 | −199.386 | −203.356 | −201.727 | −200.134 |
| region of amino acid substitutions | N/A | All regions | Surface; Unstructured, loop, and beta-sheet | Surface; Unstructured, loop, and beta-sheet | Surface; loop, and beta-sheet | Surface; Helix and loop | Surface; loop |

TABLE 4-continued structural characterization of modified MNEI based proteins

| | MNEI | DM03 E2N/I8T/N14K/ E23A/Q28K/R31T/ N35T/C41T/Y65K/ S67N/R84L | DM08 E2N/E23V/ Y65K | DM09 E2N/E23A/ Y65R | DM10 Q28K/R31T/ N35T/S67N | DM11 I8T/N14K/ C41T/R84L | DM12 I8T/C41T |
|---|---|---|---|---|---|---|---|
| % identity/similarity to MNEI (overall) | 100% | %88.542 | %96.875 | %96.875 | %95.833 | %95.833 | %97.917 |

Example 1B: Sensory Evaluation of Sweet Taste Threshold for Designer MNEI Based Proteins in Soft Drink Model Solution The purpose of this study was to assess the sweet taste threshold of the novel MNEI-based proteins and MNEI and to estimate the taste threshold of the novel proteins DM08 and DM10.

Methods:

The sweetness potency of MNEI-based proteins described herein relative to sucrose is typically in the range of 1:700 to 1:16,000. Thus, for the sake of comparison, the MNEI-based proteins and MNEI (as a reference protein) solutions were initially diluted 1:1000 and further diluted as needed. In general, the sweetness threshold of sugar for most people in soft drinks is 0.32%-1.0%. Calculations of MNEI-based proteins and MNEI (as a reference protein concentrations were carried out accordingly.

The solutions that were used in this study are detailed in Table 5. The solutions were prepared as follows: for each solution, an amount sweetener (sucrose/MNEI/Designer (modified) Protein; See Table 1 for details) was added as indicated in Table 3 and the solution was completed to 100 g with water (in order to obtain 1% sugar equivalent sweetener). 20 ml of each solution was poured into tasting cup and each sample was marked for blind testing according to Table 5.

TABLE 5

Evaluated Sweeteners

| Sweet Tasting Molecule | Estimated Conc. | Protein Purity [%] | Qnt. to add for 100 ml 1:1,000 1% Sweetness Intensity (compared to sucrose) | Samples Details & Dilution Factors |
|---|---|---|---|---|
| Sucrose - Reference sample Regular table sugar | NA | NA | 1 gr | A: water A1: 1:200 (0.5%) A2: 1:100 (1.0%) |
| MNEI | 7.5 mg/ml | >90% | | B1: 1:1,000 |
| DM08 | 2.1 mg/ml | >90% | 4.76 ml | C1: 1:1,000 |
| DM10 | 3.2 mg/ml | >90% | 3.13 ml | D1: 1:1,000 |

Test Procedure:

To evaluate the sweetness threshold for each one of the papered solutions, a double-blind taste assay was performed. The samples tested included MNEI, two MNEI designer proteins (DM08 and DM10), sucrose and mineral water. A series of concentrations were prepared by diluting the stock solution of proteins with mineral water (pH 6.9) shortly before the taste assay (Table 3). Five healthy assessors participated in this session, 2 men and 3 women, 30-50 years old of which 3 were trained tasters.

Twenty ml samples were tested randomly, in comparison to sugar solution. Before each assay, assessors were requested to rinse their mouth with water and to eat a neutral-taste cracker until no residual taste remained. The test solution was held in the mouth for at least 10 seconds. The assessors then graded the sample according to their response between 0-10; 0—no sweet perception, 10—very sweet.

The sweetness detection threshold was defined as the lowest concentration at which the taster recognized the sample as sweet. Sweetness potencies are reported relative to sucrose.

Results and Discussion

Most participates recognized the 0.5% sucrose solution as sweet with an average score of 0.63±0.6. The average score of 1% sucrose solution was 1.25±0.9, demonstrating a linear dose response (data not shown).

A similar pattern was observed for MNEI: 0.68±0.2, 0.98±0.4 and 2.2±1.0 for dilution factors of 1:4,000, 1:2,000 and 1:1,000, respectively. These results indicated that the MNEI sweetness threshold is close to 1:2,000, with sweetness potency of about 2,000 simulating 1 °Bx perception.

With regards to the MNEI designer protein DM08, a linear dose response curve was also demonstrated for dilution range between 1:12,000-1:1,000, with sweetness threshold around 1:12,000, with sweetness potency of about 10,000 simulating 1 °Bx perception.

MNEI designer protein DM10, also presented a linear curve with sweetness threshold close to 1:1,000 and sweetness potency of about 1,000 simulating 1 °Bx perception.

FIG. 1 shows a summary of the sweetness average score of solutions as described above.

Example 1C: Sensory Evaluation of Sweet Taste Threshold for MNEI in Solution

The purpose of this study was to characterize sweet MNEI-based designer proteins and to assess the sweet taste threshold, which is defined as the lowest concentration of a sweet tastant that can be detected or recognized as sweet. In this study the taste threshold of new designer MNEI-based proteins DM09, DM11 and DM12 was tested.

Methods:

As noted above, sweetness potency of sweet proteins relative to sugar depends on food composition and is typically in the range of 1:700 to 1:3,000. Consequently, the sweet protein solutions were initially diluted 1:1000 and further diluted as needed.

The sweetness threshold of sugar for most people in soft drinks is 0.32%-1.0%. Calculations of MNEI concentrations and MNEI-based proteins was carried out accordingly.

The solutions that were used in this study are detailed in Table 4. The solutions were prepared as follows: for each solution, an amount sweetener (sucrose/MNEI/Designer Protein; See Table 1 for details) was added as indicated in Table 6 and the solution was completed to 100 g with water (in order to obtain 1% sugar equivalent sweetener). 20 ml of each solution was poured into tasting cup and each sample was marked for blind testing according to Table 6.

TABLE 6

Evaluated Sweeteners

| Sweet Tasting Molecule | Estimated Conc. | Protein Purity [%] | Qnt. to add for 100 ml 1:1,000 1% Sweetness Intensity (compared to sucrose) | Samples Details & Dilution Factors |
|---|---|---|---|---|
| Sucrose - Reference sample Regular table sugar | NA | NA | 1 gr | D: water D1: 1:200 (0.5%) D2: 1:100 (1.0%) |
| MNEI previous lot reference | 5.2 mg/ml | >90% | 1 mg = 214 ul | A: 1:500 A1: 1:1,000 A2: 1:2,000 |
| DM09 | 2.97 mg/ml | >90% | 1 mg = 374 ul | E3: 1:4,000 E4: 1:8,000 E5: 1:16,000 |
| DM11 | 2.76 mg/ml | >90% | 1 mg = 403 ul | C: 1:500 C1: 1:1,000 C2: 1:2,000 |
| DM12 | 2.97 mg/ml | >90% | 1 mg = 214 ul | B: 1:500 B1: 1:1,000 B2: 1:2,000 |

Test Procedure:

To evaluate the sweetness threshold for each one of the papered solutions, a double-blind taste assay was performed. The samples tested included MNEI, two MNEI designer proteins (DM09, DM11 and DM12), sucrose and mineral water. A series of concentrations were prepared by diluting the stock solution of proteins with mineral water (pH 6.9) shortly before the taste assay (Table 6). Six healthy assessors participated in this session, 5 men and 1 woman, 30-75 years old of which half were trained tasters The sweetness detection threshold was defined as the lowest concentration at which the taster recognized the sample as sweet. Sweetness potencies are reported relative to sucrose.

Twenty ml samples were tested randomly, in comparison to sugar solution. Before each assay, assessors were requested to rinse their mouth with water and to eat a neutral-taste cracker until no residual taste remained. The test solution was held in the mouth for at least 10 seconds. The assessors then graded the sample according to their response between 0-10; 0—no sweet perception, 10—very sweet.

The sweetness detection threshold was defined as the lowest concentration at which the taster recognized the sample as sweet. Sweetness potencies are reported relative to sucrose.

Results and Discussion

Water sweetness (control) was sensed with an average value of 0.5±0.8. The non-zero value may be due to lingering effects of previous samples. All participates recognized the 0.5% sucrose solution as sweet with an average score of 1.9±0.9. The average score of 1% sucrose solution was 3.8±1.9, showing linear dose response (FIG. 1).

A similar pattern was observed for MNEI: 1.0±0.7, 2.5±1.4 and 4.7±3.2 for dilution factors of 1:2,000, 1:1,000 and 1:500, respectively. These results indicate that the MNEI sweetness threshold is between 1:1,000 to 1:2,000, with sweetness potency of about 1,000 compatible with 1 °Bx sugar solution.

With regards to the monellin Designer Protein DM11, it appears that the sweetness potency is below 500, as indicated from samples scores: 0.0±0.0, 0.3±0.8 and 0.4±0.9 for dilution factors of 1:500, 1:1,000 and 1:2,000 respectively. The monellin Designer Protein DM12 exhibited similar values 1.0 for all dilution factors, without a noticeable dose response.

Monellin Designer Protein DM09 demonstrated a linear dose response curve, indicating sweetness threshold around 1:16,000 with sweetness potency between 16,000 and 8,000 simulating 1 °Bx sugar solution.

Figure 2:
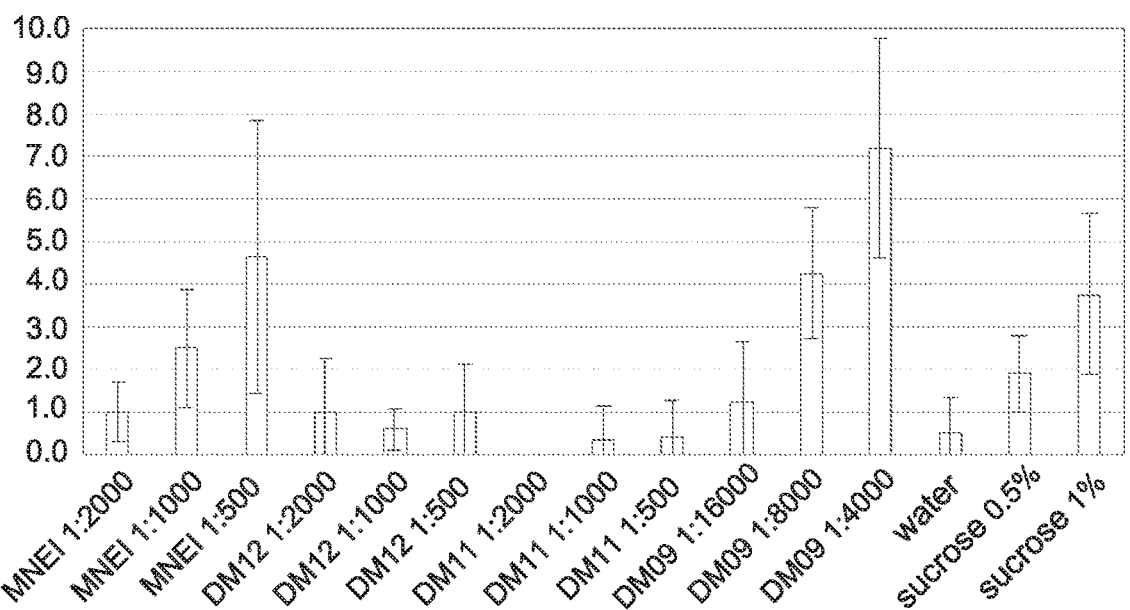
FIG. 2 is a histogram showing sweetness average score of MNEI and MNEI-based modified proteins.

The results are shown in FIG. 2.

Example 1D: Sweetness Potency of MNEI and MNEI Designer Proteins

Based on the optimization above, the sweetness potency, the aftertaste and the lingering effect of DM08 and DM09 were tested as compared with MNEI and additional sweeteners as shown in Table 7. Test method included blind testing in 6 trained participants of each one of the proteins in comparison to sugar solution.

TABLE 7

Sweetness potency of MNEI and MNEI designer proteins

| Material | Estimated Conc. | Estimated threshold concentration | Sweetness Potency at 5° BX perception | Sweetness Potency at 8° BX perception | Late onset | Lingering After Taste | Additional After Taste & Notes |
|---|---|---|---|---|---|---|---|
| Sucrose - reference sample | NA | 1 | NA | NA | No | No | No |
| Stevia REB A | NA | 1:400 | 1:250 | 1:200 | Delayed sweetness onset | Strong Sweet lingering | Bitterness & sourness |
| MNEI* | 5.22 | 1:1,500 | NA | 1:750 | Delayed sweetness onset | Sweet lingering | Low bitterness & sourness Round** profile |
| DM08 | 2.55 mg/ml | 1:10,000 | 1:9,000 | 1:3,500 | Delayed sweetness onset | Sweet lingering | Low bitterness |
| DM09 | 2.97 mg/ml | 1:15,000 | 1:11,000 | 1:4,000 | Delayed sweetness onset | Clean*** but longer sweet lingering | Slightly fruity aftertaste |

*>90% protein purity;
**Round profile means a balanced taste characteristic free from pronounced tastes or aftertastes;
***Clean profile means flavorful, but without any pungent or unusual flavors.

As can be seen, higher sweetness potency for MNEI designer proteins, compared with MNEI. It should be noted that sweetness threshold of MNEI and MNEI modified proteins, DM08 in the tested experiments is 10,000 greater than sugar by weight and that of DM09 is 15,000 greater than sugar. A non-linear dose response was demonstrated, showing that at sweetness potency at 8 °BX perception for DM08 is 3,500 greater than sugar and that of DM09 is 4,000 greater than sugar.

Further, the synergy effects were tested in blind of the various combinations in 6 participants comparison to sugar solution (Table 8).

TABLE 8

Taste Profile at 5.0° BX perception (stevia: MNEI designer protein ratio 1:1 and 0.1:1) - a synergistic effect between MNEI designer proteins and Stevia

| Material | Late onset | Lingering | Additional After Taste & Notes |
|---|---|---|---|
| Stevia REB A:DM08 (1:1) | Delayed onset reduced compared with samples that included only Stevia or DM08 (Table 7) | Sweet lingering | Slightly licorice* aftertaste Sweetness intensity higher than the reference |
| Stevia REB A:DM09 (1:1) | Delayed onset reduced compared with samples that included only Stevia or DM09 (Table 7) | Sweet lingering | Slightly sour & licorice aftertaste* Sweetness intensity higher than the reference |
| Stevia REB A:DM08 (0.1:1) | Delayed onset reduced compared with samples that included only Stevia or DM08 (Table 7) | Sweet lingering | Slightly licorice* aftertaste Sweetness intensity higher than the reference |
| Stevia REB A:DM09 (0.1:1) | Delayed onset reduced compared with samples that included only Stevia or DM09 (Table 7) | Sweet lingering | Slightly sour & licorice* aftertaste Sweetness intensity higher than the reference |

*Sense of licorice type flavor

A synergistic effect between MNEI designer proteins (DM08/DM09 and stevia (REB A)) was demonstrated for Stevia/MNEI ratio within the range of 1.0:1.0-0.1:1.0, accordingly:

The sweetness potency of stevia+MNEI designer proteins DM08 and DM09 was higher than the additive values.

The combination of MNEI designer proteins with stevia reduced the delayed onset and overall lingering and other aftertaste.

Further combinations were tested in blind comparison of the various combinations to sugar solution in 6 participants.

Table 9 shows a taste Profile at 8.0 °BX perception (3.0 °BX sugar addition) (stevia: MNEI designer protein ratio 0.1:1.0)—A Synergistic Effect between MNEI designer proteins and Stevia in the Presence of Sugar

| Material | Late onset | Lingering | After Taste |
|---|---|---|---|
| Sucrose - reference sample | No | No | No |
| Stevia REB A (3.0° BX sugar addition) | Reduced late onset | Reduced sweet lingering | |
| DM08 (3.0° BX sugar addition) | Reduced late onset | Reduced sweet lingering | |
| DM09 (3.0° BX sugar addition) | Reduced late onset | Reduced sweet lingering | |
| Stevia REB A:DM08 (1:1) (3.0° BX sugar addition) | Almost like sugar | Almost no lingering | Rounder than sugar |
| Stevia REB A:DM09 (1:1) (3.0° BX sugar addition) | Almost no late onset | Reduced sweet lingering | |
| Stevia REB A:DM08 (0.1:1) (3.0° BX sugar addition) | Almost like sugar | Almost no lingering | Rounder than sugar |
| Stevia REB A:DM09 (0.1:1) (3.0° BX sugar addition) | Almost no late onset | Reduced sweet lingering | |

All the tested samples presented a better taste performance in presence of sugar (3 °Bx), with reduced late onset and reduced lingering and other aftertastes.

The blends of Stevia/DM08 (E & G) have been highlighted for their sugar like taste profile.

TABLE 10 characterization of modified MNEI based proteins

| | MNEI | DM003 E2N/I8T/N14K/ E23A/Q28K/R31T/ N35T/C41T/Y65K/ S67N/R84L | DM008 E2N/E23V/ Y65K | DM009 E2N/E23A/ Y65R | DM010 Q28K/R31T/ N35T/S67N | DM011 I8T/N14K/ C41T/R84L | DM012 I8T/C41T |
|---|---|---|---|---|---|---|---|
| Sweetness Potency relative to MNEI | 1.0 | Not sweet at all | 6.0 | 7.5 | 0.5 | 0.2 | 0.5 |
| $T_m$ (° C.) Structural thermal stability | 69 | 81.5 | 81 | 81 | 71 | 69 | 65 |
| shelf life stability | At least 12 months at 4° C. | | At least 6 months at 4° C. | At least 6 months at 4° C. | | | |
| solubility in water | | | | Soluble | | | |

As shown, all the tested modified proteins were found to exhibit equal or improved sweetness as well as revealed sweet taste elucidated by DM12 to a similar level as MNEI, DM09 at least equal or improved melting temperature.

Example 2—Design of Thaumatin Based Proteins

Example 2A: Design of Thaumatin Based Proteins

Design of Thaumatin-based proteins was done based on SEQ ID NO:1 as a reference protein.
Computational Methods
During the CPD process, the only replacement that were allowed are the ones around the helix and the non-exposed side of the beta-sheet that forms the core of the protein. ROSETTA run had results in over 71K models. When the energy of all models was drawn, the outcome graph has the form of a logit function. Logit function (aka log-odds) is the logarithm of the odds p/(1−p) where p is the probability. It is the inverse of the sigmoidal "logistic" function.

For further analysis, the 5K lowest models were selected. Plotting the number of replacements as function of REU gave a Gaussian distribution, showing that the populations is normal and valid for further analysis. The outcome of the CPD can be seen in Table 11

TABLE 12

Summery of replacements found in CPD.

| Position | Residue in SEQ ID NO: 1 | Exposed/ Buried | Helix/ Beta/Loop | Suggested substitutions |
|---|---|---|---|---|
| 1 | A | Exposed | Beta | S |
| 2 | T | Buried | Beta | V/I |
| 3 | F | Exposed | Beta | W/F |
| 4 | E | Exposed | Beta | V/E |
| 6 | V | Partially exposed | Beta | V/Y/I |
| 8 | R | Exposed | Loop | N/M |
| 10 | S | Exposed | Loop | P |
| 30 | Q | Exposed | Beta | Q/E |
| 32 | N | Exposed | Loop | P |
| 33 | S | Exposed | Loop | P |
| 35 | E | Exposed | Beta | A |
| 36 | S | Exposed | Beta | V/T |
| 37 | W | Mostly buried | Beta | W |
| 38 | T | Exposed | Beta | V/P |
| 39 | I | Buried | Beta | A/I |
| 40 | N | Exposed | Beta | V/Y |
| 52 | A | Buried | Beta | G |
| 88 | A | Buried | Beta | A/V |
| 93 | N | Partially exposed | Beta | N/M |
| 100 | I | Buried | Beta | I/V |
| 104 | N | Buried | Loop | L/N |
| 112 | M | Buried | Beta | A/M/V |
| 113 | N | Partially exposed | Beta | K/E |
| 114 | F | Buried | Beta | V/C |
| 115 | S | Exposed | Beta | R/E |
| 117 | T | Exposed | Loop | L/A/F/K |
| 118 | T | Exposed | Loop | T/D |
| 119 | R | Exposed | Loop | T |
| 124 | V | Buried | Beta | A/S |
| 125 | R | Exposed | Beta | E |
| 127 | A | Exposed | Loop | S/D |
| 128 | A | Exposed | Loop | S |
| 129 | D | Exposed | Loop | P |
| 131 | V | Exposed | Helix | E |
| 132 | G | Exposed | Helix | K/D |
| 133 | Q | Exposed | Helix | Q/N |
| 136 | A | Exposed | Helix | P |
| 137 | K | Exposed | Helix | D/S |
| 139 | K | Exposed | Loop | R |
| 140 | A | Exposed | Loop | H |
| 142 | G | Exposed | Loop | G/E |
| 148 | A | Buried | Helix | P |
| 152 | F | Exposed | Helix | Y/F |
| 154 | T | Exposed | Loop | Q |
| 157 | Y | Exposed | Helix | Y/H |

TABLE 12-continued

Summery of replacements found in CPD.

| Position | Residue in SEQ ID NO: 1 | Exposed/ Buried | Helix/ Beta/Loop | Suggested substitutions |
|---|---|---|---|---|
| 165 | G | Exposed | Loop | G/T |
| 166 | P | Partially exposed | Loop | P/A |
| 168 | E | Exposed | Helix | E/D/P |
| 169 | Y | Partially exposed | Helix | A |
| 171 | R | Exposed | Helix | K |
| 172 | F | Partially exposed | Helix | Y/F |
| 175 | R | Exposed | Helix | K/L |
| 176 | L | Exposed | Helix | L/N |
| 179 | D | Exposed | Loop | E |
| 191 | V | Partially exposed | Beta | V/Q/W |
| 196 | S | Exposed | Loop | G |
| 197 | S | Exposed | Loop | A |
| 198 | N | Exposed | Loop | R/H/N |
| 200 | R | Exposed | Beta | E/R |
| 202 | T | Partially exposed | Beta | I/V |
| 206 | T | Exposed | Loop | N/R |
| 207 | A | Exposed | Loop | T/I |

Example 2B: Expression of Thaumatin Modified Proteins in *Pichia pastoris* (Currently Termed *Komagataella phaffi*)

Six thaumatin variants were tested for expression and secretion from the yeast *P. pasoris*, utilizing two different induction systems, namely methanol driven and glucose driven expression. The sequences and expression systems are depicted in the Table 12 below.

TABLE 12 sequences and expression systems

| SEQ ID NO: | Denoted as | Induction by |
|---|---|---|
| 21 | TM1 | Methanol |
| 23 | TM2 | Methanol |
| 25 | TM3 | Methanol |
| 27 | TM4 | Glucose |
| 29 | TM5 | Glucose |
| 31 | TM6 | Glucose |

Figure 3:
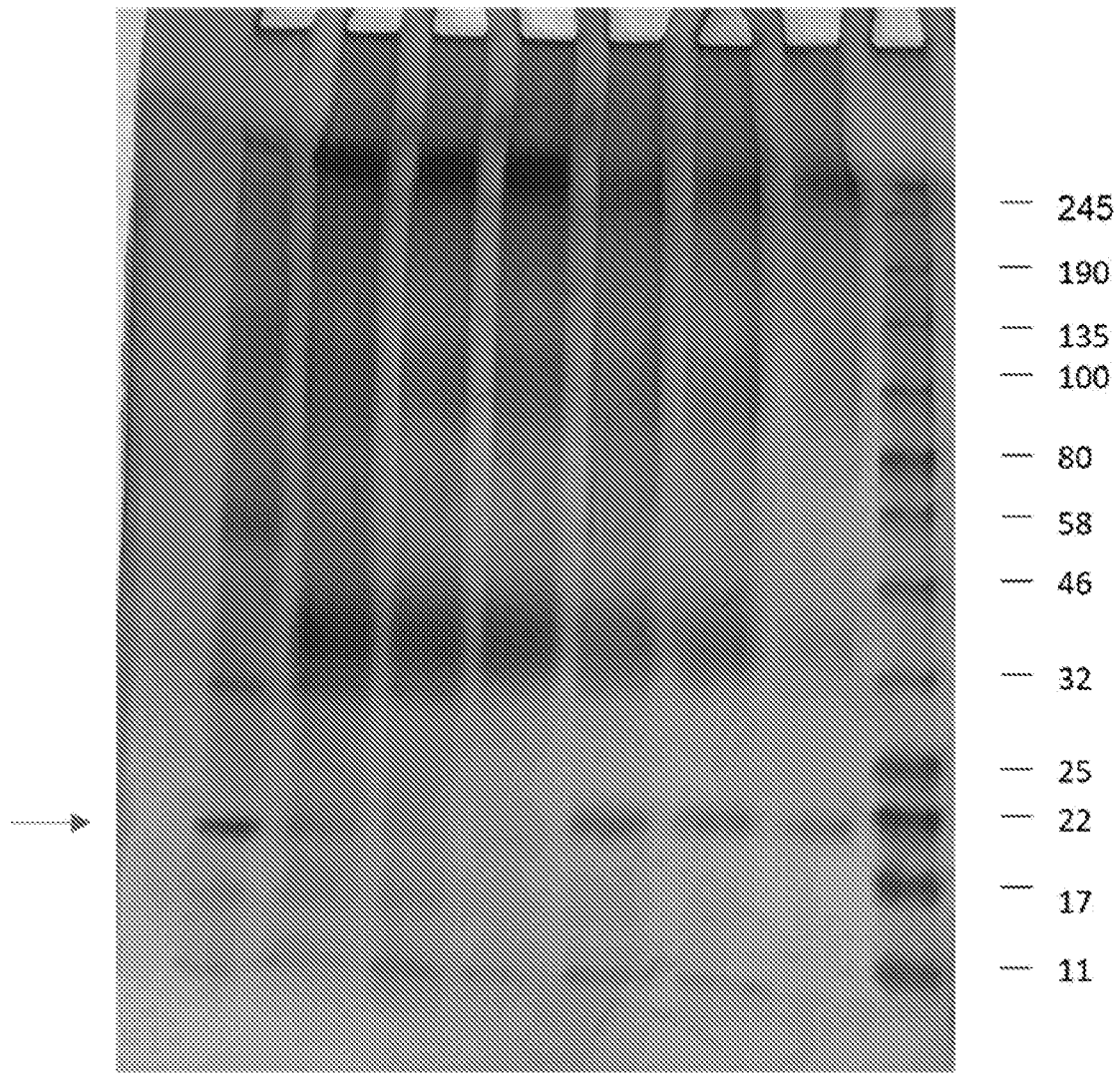
FIG. 3 is an acryl amide gel of expression experiments in pichia strain.

Expression was tested in X33, or LP1 pichia strains following electroporation and selection by zeocin (500-1000 μg/ml). Example of result can be seen in FIG. 3, presenting culture conditioned medium separated by acryl amide gel. Condition medium from selected colonies separated by acryl amide gel electrophoresis and detected by silver stain. Cosmatin (lanes 2-7) is detected at the correct molecular weight of 22 kDal (arrow). Secretion is driven by amylase (T8-1) or alpha mating factor (2) signal sequences. Lane 1—Thaumatin expression under the same conditions, secretion driven by thaumatin "pre" signal sequence (MAAT-TCFFFLFPFLLLLTLSRA).

Experiments were conducted with three different host organism strains including X-33, GS115 and LP1. Expression systems included both methanol induction (with promotor AOX1, tested in strains X33, GS115 and LP1) and glucose induction (with promotor G1-3, tested in strains LP1 and GS115).

Different signal peptides were screened. For AOX1 these include aAmylase, alphaK, alphaT, Glucoamyl, inulinase, invertase, killerpro, lysozyme, albumin and pre-thaumatin. For G1-3 these include pre-thamatin, LSP1, LSP2 and alphaMF.

In the case of thaumatin, the lowest pseudo-energy score received by the CPD software included 54 substitutions. Though, following cross-validation by numerous orthogonal methods, some modified proteins expressed in the lab included 3 and 22 substitutions. Orthogonal methods include sequence- and structural conservation within the computer-derived models as well as within the evolutionary family of the protein, analysis of hydrophobic patches, cavities, dynamic high- and low-temperature dynamics (as assessed e.g. by molecular dynamics), visualization, correspondence to known mutations and alike. ~72,000 models and the pseudo-energy (scoring function) distribution. Each model is a different sequence and all pseudo-energies are below that of the input (wild-type) protein. Focus on the 5,000 lowest pseudo-energy models: Pseudo-energy vs. number of substitutions (computer output before scoring and validation by orthogonal methods)

Example 3: Characterization of Receptor Binding Site

Characterization of the receptor binding site comprising at least the following amino acids, wherein A corresponds to TAS1R2 (from human) and B corresponds to TAS1R3 (from human), wherein the numbering corresponds to the corresponding residue (amino acid) in the corresponding sequence:

TABLE 13

Characterization of the receptor binding site

| Amino acid | subunit |
|---|---|
| 203 | A |
| 212 | A |
| 220 | B |
| 204 | A |
| 483 | A |
| 226 | A |
| 233 | A |
| 207 | B |
| 236 | B |
| 258 | A |
| 249 | A |
| 233 | B |
| 496 | B |
| 262 | B |
| 256 | A |
| 240 | B |
| 224 | B |
| 191 | B |
| 317 | A |
| 239 | A |
| 318 | A |
| 230 | A |
| 261 | B |
| 234 | B |
| 225 | A |
| 231 | B |
| 265 | A |
| 315 | A |
| 205 | A |
| 484 | A |
| 254 | A |
| 228 | B |
| 221 | A |
| 205 | B |
| 231 | A |
| 265 | B |
| 237 | A |

TABLE 13-continued

Characterization of the receptor binding site

| Amino acid | subunit |
|---|---|
| 217 | A |
| 208 | B |
| 294 | A |
| 268 | A |
| 290 | A |
| 266 | A |
| 228 | A |
| 267 | B |
| 475 | A |
| 292 | A |
| 232 | B |
| 314 | A |
| 479 | A |
| 255 | A |
| 202 | A |
| 229 | A |
| 257 | A |

In addition, the receptor binding site comprising at least the following amino acids, wherein A corresponds to TAS1R2 (from human) and B corresponds to TAS1R3 (from human), wherein the numbering corresponds to the corresponding residue (amino acid) in the corresponding sequence (Table 14).

TABLE 14

Characterization of the receptor binding site

| Amino acid | subunit |
|---|---|
| 77 | B |
| 249 | B |
| 314 | B |
| 127 | A |
| 467 | B |
| 48 | B |
| 382 | B |
| 290 | B |
| 437 | A |
| 380 | B |
| 369 | B |
| 122 | B |
| 343 | B |
| 63 | B |
| 132 | A |
| 61 | B |
| 348 | B |
| 65 | B |
| 307 | B |
| 350 | B |
| 117 | A |
| 425 | A |
| 330 | B |
| 254 | B |
| 386 | B |
| 56 | B |
| 357 | B |
| 308 | B |
| 174 | A |
| 363 | B |
| 413 | A |
| 401 | A |
| 435 | A |
| 346 | B |
| 385 | B |
| 349 | B |
| 47 | B |
| 124 | A |
| 364 | B |
| 67 | B |
| 355 | B |
| 342 | B |

TABLE 14-continued

Characterization of the receptor binding site

| Amino acid | subunit |
|---|---|
| 414 | A |
| 375 | B |
| 311 | B |
| 339 | B |
| 404 | A |
| 354 | B |
| 125 | A |
| 59 | B |
| 358 | B |
| 289 | B |
| 362 | B |
| 440 | A |
| 366 | B |
| 129 | A |
| 465 | B |
| 426 | A |
| 123 | B |
| 428 | A |
| 371 | B |
| 252 | B |
| 372 | B |
| 360 | B |
| 54 | B |
| 317 | B |
| 130 | A |
| 341 | B |
| 464 | B |
| 32 | B |
| 345 | B |
| 53 | B |
| 291 | B |
| 253 | B |
| 379 | B |
| 313 | B |
| 359 | B |
| 463 | B |
| 356 | B |
| 412 | A |

The receptor binding site comprising at least the following amino acids, wherein A corresponds to TAS1R2 (from human) and B corresponds to TAS1R3 (from human), wherein the numbering corresponds to the corresponding residue (amino acid) in the corresponding sequence (Table 15).

TABLE 15

Characterization of the receptor binding site

| Amino acid | subunit |
|---|---|
| 77 | B |
| 120 | B |
| 128 | B |
| 380 | B |
| 135 | B |
| 369 | B |
| 122 | B |
| 343 | B |
| 348 | B |
| 350 | B |
| 417 | B |
| 333 | B |
| 34 | B |
| 357 | B |
| 336 | B |
| 363 | B |
| 411 | B |
| 346 | B |
| 349 | B |
| 124 | A |
| 87 | B |
| 364 | B |
| 94 | B |
| 355 | B |
| 342 | B |
| 409 | B |
| 339 | B |
| 354 | B |
| 125 | A |
| 358 | B |
| 362 | B |
| 366 | B |
| 123 | B |
| 420 | B |
| 85 | B |
| 88 | B |
| 412 | B |
| 332 | B |
| 133 | B |
| 360 | B |
| 341 | B |
| 413 | B |
| 121 | B |
| 32 | B |
| 345 | B |
| 379 | B |
| 92 | B |
| 359 | B |
| 418 | B |
| 356 | B |

Figure 4C:
FIGS. 4A to 4C are representations of the three binding sites of receptor of Thaumatin docking to the TAS1R2 and TAS1R3.
Figure 4B:
Figure 4A:
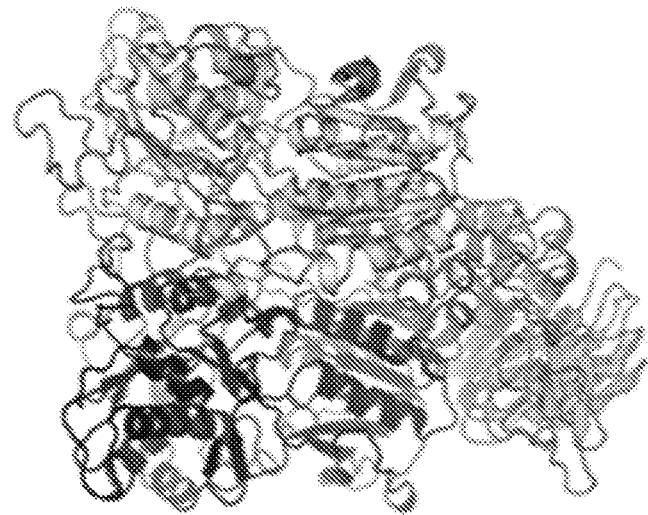

FIG. 4A to 4C show representations of the suggested binding sites. Following simulations of thaumatin docking to the receptor, three high-probability binding sites were found on the receptor. During the simulation numerous docking prediction experiments are conducted and the low-energy results are clustered. FIG. 4A to 4C depict the three sites and the thaumatin clustering on these sites.

The invention claimed is:

1. A modified protein comprising an amino acid sequence having amino acid replacements at residues corresponding to residues E2, E23, and Y65 of a reference protein, wherein the modified protein has improved sweetness and increased thermal stability, as defined by Differential Scanning Fluorometry, compared to the reference protein, wherein the modified protein has improved functional thermal stability relative to the reference protein and relative to the reference protein modified at only two of residues E2, E23, and Y65, and wherein the reference protein comprises the sequence set forth in SEQ ID NO:5.

2. The modified protein according to claim 1, having at least 1.5 fold increased sweetness potency compared with the reference protein.

3. The modified protein according to claim 1, having at least six fold increased sweetness potency compared with the reference protein.

4. The modified protein according to claim 1, further characterized by at least one of the following compared with the reference protein: (1) increased pH stability, (2) an increased solubility, and (3) increased shelf life stability.

5. The modified protein according to claim 1, wherein the amino acid substitution at residue E2 is selected from the group consisting of E2N, E2D, E2Q, E2R, and E2K; the amino acid substitution at residue E23 is selected from the group consisting of E23A, E23N, E23D, E23Q, E23R, and E23K; and the amino acid substitution at residue Y65 is selected from the group consisting of Y65F, Y65W, Y65H, Y65V, Y65I, Y65L, Y65M, Y65C, Y65A, Y65T, Y65S, Y65P, Y65G, Y65K and Y65R.

6. The modified protein according to claim 5, wherein the amino acid substitutions comprise E2N; E23V or E23A; and Y65K or Y65R.

7. The modified protein according to claim 1, having an amino acid sequence set forth in SEQ ID NO:16 or SEQ ID NO:17.

8. The modified protein according to claim 1, wherein the modified protein comprises amino acid substitutions E2N, E23A, and Y65R.

9. The modified protein according to claim 1, wherein the modified protein comprises amino acid substitutions E2N, E23V, and Y65R.

* * * * *